(12) United States Patent
Gerritsen et al.

(10) Patent No.: US 6,858,427 B2
(45) Date of Patent: Feb. 22, 2005

(54) SPHINGOSINE KINASES

(75) Inventors: Mary E. Gerritsen, San Mateo, CA (US); Luca Rastelli, Guilford, CT (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/784,810

(22) Filed: Feb. 14, 2001

(65) Prior Publication Data

US 2002/0082203 A1 Jun. 27, 2002

Related U.S. Application Data

(60) Provisional application No. 60/191,261, filed on Mar. 22, 2000, and provisional application No. 60/182,360, filed on Feb. 14, 2000.

(51) Int. Cl.$^7$ .................. C12N 15/52; C12N 15/54; C12N 15/63

(52) U.S. Cl. ................. 435/325; 435/320.1; 435/252.3; 435/455; 435/471; 536/23.1; 536/23.2; 536/23.5

(58) Field of Search ............................... 536/23.1, 23.2, 536/23.5; 435/320.1, 325, 252.3, 455, 471; 514/44

(56) References Cited

FOREIGN PATENT DOCUMENTS

WO   WO 9854963 A2 * 12/1998

OTHER PUBLICATIONS

Orkin et al., Report and Recommendations of the Panel to Access the NIH Investment in Research on Gene Therapy, issued by the US NAtional Institutes of Health, Bethesda, MD, Dec. 1995.*
Verma et al., "Gene therapy—promises, problems, and prospects," Nature 389: 239–242, 1997.*
Rosenberg et al., "Gene therapist, heal thyself," Science 287 : 1751, Mar. 10, 2000.*
Kennell, D. E., "Principles and practices of nucleic acid hybridization," Prog. Nucl. Acid Res. Mol. Biol. 11: 259–310, 1971.*
Rudinger, J., "Characteristics of the amino acids as components of a peptide hormone sequence," in (Parsons, J.A., ed.) Peptide Hormones, Univ. Park Press: Baltimore, MD, 1976, pp. 1–7.*
Ngo et al., "Computational complexity, protein structure prediction, and the Levinthal paradox," in (Merz et al., eds.) The Protein Folding Problem and Tertiary Structure Prediction, Birhauser: Boston, MA, 1994, pp. 433, 492–495.*

Kohama et al. (Kohama T, Olivera A, Edsall L, Nagiec MM, Dickson R, Spiegel S. "Molecular cloning and functional characterization of murine SphK". *J. Biol. Chem.*, Sep. 11, 1998:273(37):23722.
Ortmeyer, J. and V. Mohsenin, *Life Sci* 1996; 59(3):255–262, Inhibition of Phospholipase D and superoxide generation by glucose in diabetic neutrophils.
Wang et al *Cancer Res.*, Dec. 15, 1999, 59(24):6185–91, Sphingosine–1–phosphate inhibits motility of human breast cancer cells independently of cell surface receptors.
Xia et al., *J. Biol. Chem.*, Nov. 26, 1999;274(48):34499–505, Activation of SphK by tumor necrosis factor–alpha inhibits apoptosis in human endothelial cells.
Anderson, J.V., GenBank Acc. BI946369, Oct. 19, 2001.
Lee, N.H., GenBank Acc. AI237625, Jan. 31, 1999.
Ann. By the C.elegans Genome Sequencing Consortium, GenBank Acc. NM 059576, Dec. 3, 2001.
Kohama, T., et al., GenBank Acc. AF068748, Sep. 29, 1998.
Strausberg, R., Ph.D., GenBank Acc. AI478197, Apr. 14, 1999.
Nakamura, Y., GenBank Acc. D31133, Feb. 1995.
Wilson, R.K., GenBank Acc. AA026479, May 1997.
Wilson, R.K., GenBank Acc. AA232791, Aug. 1997.
Strausberg, R., Ph.D., GenBank Acc. AI769914, Dec. 21, 1999.
Strausberg, R., Ph.D., GenBank Acc. AI972156, Mar. 8, 2000.
Wilson, R.K., GenBank Acc. AA081152, Dec. 1996.
Bates, K., GenBank Acc. AL096766, Jan. 7, 2000.
Bates, K., GenBank Acc. CAB62977, Jan. 7, 2000.
Marra, M., GenBank Acc. AI536375, Mar. 15, 2000.

* cited by examiner

*Primary Examiner*—Scott D. Priebe
(74) *Attorney, Agent, or Firm*—Merchant & Gould P.C.

(57) ABSTRACT

Disclosed herein are novel human nucleic acid sequences that encode polypeptides. Also disclosed are polypeptides encoded by these nucleic acid sequences, and antibodies that immunospecifically-bind to the polypeptide, as well as derivatives, variants, mutants, or fragments of the aforementioned polypeptide, polynucleotide, or antibody. The invention further discloses therapeutic, diagnostic and research methods for diagnosis, treatment, and prevention of disorders involving any one of these novel human nucleic acids and proteins.

11 Claims, 6 Drawing Sheets

MULTIPLE ALIGNMENT:
SPI MULTIPLE ALIGNMENT:
CA
SPI
CA SPkinaseinHSDA59H18  MEKPYAFTVHCVKRARRHRWKWAQVTFWCPBEQLCHLWLQTLRBMLEKLTSRPKHLLVFI
SPI CAB62977                                                               PKHLLVFI CA SPkinaseinHSDA59H18  NPFGGKGQGKRIYERKVAPLFTLASITTDIIGNKFYVNYVEVITEHANQAKETLYEINID
SPI CAB62977            NPFGGKGQGKRIYERKVAPLFTLASITTDIIGNKFYVNYVEVITEHANQAKETLYEINID CA SPkinaseinHSDA59H18  KYDGIVCVGGDGMFSEVLHGLIGRTQRSAGVDQNHPRAVLVPSSLRIGIIPAGSTDCVCY
SPI CAB62977            KYDGIVCVGGDGMFSEVLHGLIGRTQRSAGVDQNHPRAVLVPSSLRIGIIPAGSTDCVCY CA SPkinaseinHSDA59H18  STVGTSDAETSALHIVVGDSLAMDVSSVHHNSTLLRYSVSLLGYGFYGDIIKDSEKKRWL
SPI CAB62977            STVGTSDAETSALHIVVGDSLAMDVSSVHHNSTLLRYSVSLLGYGFYGDIIKDSEKKRWL CA SPkinaseinHSDA59H18  GLARYDFSGLKTFLSHHCYEGTVSFLPAQHTVGSPRDRKPCRAGCFVCRQSKQQLEEEQK
SPI CAB62977            GLARYDFSGLKTFLSHHCYEGTVSFLPAQHTVGSPRDRKPCRAGCFVCRQSKQQLEEEQK CA SPkinaseinHSDA59H18  KALYGLEAABDVEEWQVVCGKFLAINATNMSCACRRSPRGLSPAAHLGDGSSDILIRKC
SPI CAB62977            KALYGLEAABDVEEWQVVCGKFLAINATNMSCACRRSPRGLSPAAHLGDGSSDLLLIRKC CA SPkinaseinHSDA59H18  SRFNFLRFLIRHTNQQDQFDFTEVEVYRVKKPQFTSKHMEDEDSDLKEGGKKRFGHICSS
SPI CAB62977            SRFNFLRFLIRHTNQQDQ SPkinaseinHSDA59H18  HPSCCCTVSNSSWNCDGE

MULTIPLE ALIGNMENT:

```
52180312           ------------------------------------------------------------
AI237625           ------------------------------------------------------------
SPkinaseinHSDA59H18 PKHLLVFINPFGGKGQGGKRIYERKVAPLFTLASITTDIIGNKFYVNYVEVITEHANQAKE 52180312           ------------------------------------------------------------
AI237625           ------------------------------------------------------------
SPkinaseinHSDA59H18 TLYEINIDKYDGIVCVGGDGMFSEVLHGLIGRTQRSAGVDQNHPRAVLVPSSLRIGIIPA 52180312           ------------------------------------------------------------
AI237625           ------------------------------------------------------------
SPkinaseinHSDA59H18 GSTDCVCYSTVGTSDAETSALHIVVGDSLAMDVSSVHHNSTLLRYSVSLLGYGFYGDIIK 52180312           ------------------------------------------------------------
AI237625           ------------------------------------------------------------
SPkinaseinHSDA59H18 DSEKKRWLGLARYDFSGLKTFLSHHCYEGTVSFLPAQHTVGSPRDRKPCRAGCFVCRQSK 52180312           ------------------------------------------------------------
AI237625           ------------------------------------------------------------
SPkinaseinHSDA59H18 QQLEEEQKKALYGLEAAEDVEEWQVVCGKFLAINSTNMSCAQRSPRGLSPAAHLGDGSS 52180312           ------------------YRVKKFLFTSKHVEDEDNDSKEQEKQ
AI237625           ------------------------FTEVEVYRVKKFQFTSKHVEDDDNDLKELEKQ
SPkinaseinHSDA59H18 FLAINSTNMSCAQPRSPEGLSAFAAHLGDSSFTEVEVYRVKKFQFTSKHMEDEDSDLKEGGKK 52180312           DLLIRKCSRFNFLRFLIRHTNQEDQFASRSSWNCDGEVMHSPAIEVRHCQLVRLFARGIEEES-----
AI237625           DLLIRKCSRFNFLRFLIRHTNQQDQFSRSSWNCDGEVLHSPAIEVRHCQLVRLFARGIEEES-----
SPkinaseinHSDA59H18 KFGKICKDRPSCTQSASRSSWNCDGEVMHSPAIEVRHCQLVRLFARGIEEES-----
                    KFGQICKDNPECAQPTSRSSWNCDGEVLHSPAIEVRHCQLVRLFARGIEEES-----
                    RFGHICSSHPSCCCIMSNSSWNCDGEVLHSPAIEVRHCQLVRLFARGIEENPKPDSHS
```

```
SPkinaseinHSDA59H18      ----------------------------------MEKPY-----------------------------AFTVHCVKRARRRWKWAQVT
coorected_human_sphingosine ----------------------------------MDPAGGPRGVLPRPC--------------------RVEVLLINPRGGKGKALQEFR
AF068748_EXT-2           ----------------------------------MEIVEIPRGLLPRPC--------------------RVEVLIINPQGGKGKALQEFQ
Q06147                   LYIDYDPHSS-SHLDEE----DDLVEEILKRSYKNTRRNK-SIEVVLINPFSGKGKAKLFM
Q12246                   LLIDHVSRKSRANTGEENISSGTVEEIEKSYENSKRNR-SIEIVLINHHGGKGGTAKNEEL
O14159                   CWVDFVENSD--------QFCEYLEDVAYKGIKRSR-RFIVFINPHGGKGKAWHIWE
O18425                   CRSDAEENEQ------------LTSVIISRKPPPQEQCRGNLEVFENSGIGKSLETEPA
SPkinaseinHSDA59H18      FWCPBEQLCH------------LWLQTLREMLEKLTSRPK-HLIVFINPHFGGKGQGKRIYE
                                                                              C1 coorected_human_sphingosine SHVDPLLAEEHSFTLMLLER-----------RNHARELVR------SEEIGRWMDALVMSGDGLM
AF068748_EXT-2           SRMDPFFEEPELHFKLILLER-----------KMHARELVC------ABEIGHWBAIAVMSGDGLM
Q06147                   TKAKPLILASRCSIEVVTKY-----------PGHATEIAR------EMDIDKVEDLTACASGDGIP
Q12246                   TKARPILEVESGCKIEHAYEKY-----------ARHIDIPAK------DLEISKVDILACASCDGIP
O14159                   SEAEDVFSSEHSICEWVTER-----------KDIHADSIAK------NLEVSSNGDGLTSVGGDGEF
O18425                   NTNGRKIEDKSLERYEVVIEG-----------PNHARNLMT------KADLSKFNGVLIILSGDGEV
SPkinaseinHSDA59H18      RKVAPLFTLASHIITDIIGNKFYVNYVEVITEIANQAKETLYEI NIDKVDSINVCGGDGMF
                                                                              C2 coorected_human_sphingosine METAIQKPLCSLPA-SCNATAASINHYPAGYEQVINEDLLTNGIIEL
AF068748_EXT-2           METAIQKPLCSIPGLCSSGNIAASINHYPAGYEQVINEDLLINGIIEL
Q06147                   VKAFNMTAITELPCSSGNAMSVS-CHWIN--------NPSYSTLGIIK
Q12246                   VDAFNKLAVTQLPCCSSGNAMSIS-CHWIN--------NPSYAALGIVK
O14159                   VLEAFKHFVCMIPGSSGNAFSYN-------AIG--------QLKPALTALEIEK
O18425                   FRIFPTLFHGIVPSSGNLLGLLCSVLSKYCTKMNEKSVMERALETA
SPkinaseinHSDA59H18      SEVLHGILGHGRTQRSAGVDQNGPRAVLVFSSLRIGIIPAGSTDCVCYSTVGTSDAETSAEH
                                                                              C3 coorected_human_sphingosine LCRPVLSPMNLLSLHTASGLRSFSMVFSLAMGFMADVDLESDKIR-REGEMRFTEGTIRTI
AF068748_EXT-2           LCRRRLSPMNLLSLHTASGLRLMSF-SLSWGFMADVDLESEKYR-REGEIRFTVSEIEFI
Q06147                   SIETRIDLMCCSQPSYAREHPKLSFLSQTVGILAETDINIEFIR-WMGPARFEEGVAFNI
Q12246                   SIETRIDIMCCSQPSYMNEWPRLSFLSQTVGVILAESDINIEFIR-WMGPVRENEGVAFNI
O14159                   GRPLIFSFKLMTFEQ----KGKKAMSFEIANVLGIIAEQDIGIENWR-FMGENRAYLGFFIRL
O18425                   TSPLAKAESVALYSVKTDNQSYAFSFSTGWLMADEIDIDSEKMRLSEGHRETVMGFIIRS
SPkinaseinHSDA59H18      IVVGDSLAMDVSSVHHNSTLLRMSVSLIGVGFYGEHIIDSEKRILMIGLARMDFSGLKTF
                                                                              C4
```

FIG. 3

| FIG. 3A | FIG. 3B |
|---------|---------|

FIG. 3B

PHYLIP - PROTEIN DISTANCE ANALYSIS

SEQUENCES ANALYZED:

1. SPkinaseinHSDA59H18
2. Q18425
3. O14159
4. Q06147
5. Q12246
6. coorected_human_sphingosine
7. AF068748_EXT-2

7 POPULATIONS

NEIGHBOR-JOINING/UPGMA METHOD VERSION 3.572c

NEIGHBOR-JOINING METHOD

NEIGHBOR BRANCH LENGTHS ALLOWED

REMEMBER: THIS IS AN UNROOTED TREE!

| BETWEEN | AND | LENGTH |
|---|---|---|
| 5 | 3 | 1.09970 |
| 3 | 1 | 1.59865 |
| 1 | Q06147 | 0.79847 |
| 1 | Q12246 | 1.02742 |
| 3 | O14159 | 1.74537 |
| 5 | Q18425 | 4.00995 |
| 5 | 4 | 0.43259 |
| 4 | 2 | 1.44382 |
| 2 | coorected_ | 0.24774 |
| 2 | AF068748_E | 0.37392 |
| 4 | SPkinasein | 5.26443 |

MULTIPLE ALIGNMENT:

```
80432911          AGAPGADACSVPVSELIAVEETDVHGKHQGSGKWQKMEKPYAFTVHCVKRARRHRWKWAQ
SPkinaseinHSDA59H18 ------------------------------MEKPYAFTVHCVKRARRHRWKWAQ 80432911          VTFWCPEEQLCHLWLQTLREMLEKLTSRPKHLLVFINPFGGKGQGKRIYERKVAPLFTLA
SPkinaseinHSDA59H18 VTFWCPEEQLCHLWLQTLREMLEKLTSRPKHLLVFINPFGGKGQGKRIYERKVAPLFTLA 80432911          SITTDII------VIEHANQAKETLYEINIKDYDGIVCVGGDGMFSEVLHGLIGR
SPkinaseinHSDA59H18 SITTDIIGNKFYVNYVEVITEHANQAKETLYEINIKDYDGIVCVGGDGMFSEVLHGLIGR 80432911          TQRSAGVDQNHPRI------
SPkinaseinHSDA59H18 TQRSAGVDQNHPRAVLVPSSLRIGIIPAGSTDCVCYSTVGTSDABTSALHIVVGDSLAMD 80432911          VSSVHHNSTLLRYSVSLIGYGFYGDIIKDSEKKRWLGLARYDFSGLKTFLSHHCYEGTVS
SPkinaseinHSDA59H18

80432911          FLPAQHTVGSPRDRKPCRAGCFVCROSKQOLEEEQKKALYGLEAAEDVEEWQVCGKFLA
SPkinaseinHSDA59H18

80432911          INATNMSCACRRSSPRGLSPAAHLGDGSSDLILIIRKCSRFNFLRFLIRHTNQQDQFDFTFV
SPkinaseinHSDA59H18

80432911          EVYRVKKFQFTSKHMEDEDSDLKEGGKKRFGHICSSHPSCCCTVSNSSWNCDGEVLHSPA
SPkinaseinHSDA59H18

80432911          IEVRVHCQLVRLFARGIEENPKPDSHS
SPkinaseinHSDA59H18
```

FIG. 5

SEQUENCE LISTING

```
<160> NUMBER OF SEQ ID NOS: 29

<210> SEQ ID NO 1
<211> LENGTH: 1600
<212> TYPE: DNA
<213> ORGANISM: Homo sapiens
<220> FEATURE:
<221> NAME/KEY: modified_base
<222> LOCATION: (1)
<223> OTHER INFORMATION: a, t, c, g, other or unknown

<400> SEQUENCE: 1
nccccccggg gctcctatag ccacggctcc gggcggggaa ggcgagcccc acagccggcc      60
ctgcgacgcc cgcctgggca gcaccgataa ggagctgaag gcaggagccg ccgccacggg     120
cagcgccccc acagcgccag ggacccctg gcagcgggag ccgcgggtcg aggttatgga     180
tccagcgggc ggcccccggg gcgtgctccc gcggccctgc cgcgtgctgg tgctgctgaa     240
cccgcgcggc ggcaagggca aggccttgca gctcttccgg agtcacgtgc agccccttt     300
```

-continued

```
ggctgaggct gaaatctcct tcacgctgat gctcactgag cggcggaacc acgcgcggga     360
gctggtgcgg tcggaggagc tgggccgctg ggacgctctg gtggtcatgt ctggagacgg     420
gctgatgcac gaggtggtga acgggctcat ggagcggcct gactgggaga ccgccatcca     480
gaagcccctg tgtagcctcc cagcaggctc tggcaacgcg ctggcagctt ccttgaacca     540
ttatgctggc tatgagcagg tcaccaatga agacctcctg accaactgca cgctattgct     600
gtgccgcccg gtgctgtcac ccatgaacct gctgtctctg cacacggctt cggggctgcg     660
ctcgttctct gtgctcagcc tggcctgggg cttcattgct gatgtggacc tagagagtga     720
taagtatcgg cgtctggggg agatgcgctt cactctgggc accttcctgc gtctggcagc     780
cctgcgcacc taccgcggcc gactggctac cctccctgta ggaagagtgg gtttcaagac     840
acctgcttcc cccgttgtgg tccagcaggg cccggtagat gcacacctgg tgccactgga     900
ggagcaggtg ccttctcact ggcaggtggt gcccgacgag gactttgtgc tagtcctggc     960
actgctgcac tcgcacctgg ccagtgagat gtttgctgca cccatgggcc gctgtgcagc    1020
tggcgtcatg catctgttct acgtgcgggc gggagtgtct cgtgccatgc tgctgcgcct    1080
cttcctggcc atggagaagg gcaggcatat ggagtatgaa tgcccctact ggtatatgt    1140
gcccgtggtc gccttccgct ggagcccaa ggatgggaaa ggtgtgtttg cagtggatgg    1200
ggaattgatg gttagcgagg ccgtgcaggg ccaggtgcac ccaaactact tctggatggt    1260
cagcggttgc gtggagcccc cgcccagctg gaagcccag cagatgccac cgccagaaga    1320
gcccttatga cccctgggcc gcgctgtgcc ttagtgtcta cttgcaggac ccttcctcct    1380
tccctagggc tgcagggcct gtccacagct cctgtggggg tggaggagac tcctctggag    1440
aagggtgaga aggtggaggc tatgctttgg ggggacaggc cagaatgaag tcctgggtca    1500
ggagcccagc tggctgggcc cagctgccta tgtaaggcct tctagtttgt tctgagaccc    1560
ccaccccacg aaccaaatcc aaataaagtg acattcccaa                          1600
```

<210> SEQ ID NO 2
<211> LENGTH: 384
<212> TYPE: PRT
<213> ORGANISM: Homo sapiens

<400> SEQUENCE: 2

```
Met Asp Pro Ala Gly Gly Pro Arg Gly Val Leu Pro Arg Pro Cys Arg
  1               5                  10                  15

Val Leu Val Leu Leu Asn Pro Arg Gly Gly Lys Gly Lys Ala Leu Gln
             20                  25                  30

Leu Phe Arg Ser His Val Gln Pro Leu Leu Ala Glu Ala Glu Ile Ser
         35                  40                  45

Phe Thr Leu Met Leu Thr Glu Arg Arg Asn His Ala Arg Glu Leu Val
     50                  55                  60

Arg Ser Glu Glu Leu Gly Arg Trp Asp Ala Leu Val Val Met Ser Gly
 65                  70                  75                  80

Asp Gly Leu Met His Glu Val Val Asn Gly Leu Met Glu Arg Pro Asp
                 85                  90                  95

Trp Glu Thr Ala Ile Gln Lys Pro Leu Cys Ser Leu Pro Ala Gly Ser
            100                 105                 110

Gly Asn Ala Leu Ala Ala Ser Leu Asn His Tyr Ala Gly Tyr Glu Gln
        115                 120                 125

Val Thr Asn Glu Asp Leu Leu Thr Asn Cys Thr Leu Leu Leu Cys Arg
    130                 135                 140

Pro Val Leu Ser Pro Met Asn Leu Leu Ser Leu His Thr Ala Ser Gly
145                 150                 155                 160
```

```
Leu Arg Ser Phe Ser Val Leu Ser Leu Ala Trp Gly Phe Ile Ala Asp
                165                 170                 175

Val Asp Leu Glu Ser Asp Lys Tyr Arg Arg Leu Gly Glu Met Arg Phe
            180                 185                 190

Thr Leu Gly Thr Phe Leu Arg Leu Ala Ala Leu Arg Thr Tyr Arg Gly
        195                 200                 205

Arg Leu Ala Thr Leu Pro Val Gly Arg Val Gly Phe Lys Thr Pro Ala
    210                 215                 220

Ser Pro Val Val Gln Gln Gly Pro Val Asp Ala His Leu Val Pro
225                 230                 235                 240

Leu Glu Glu Gln Val Pro Ser His Trp Gln Val Pro Asp Glu Asp
                245                 250                 255

Phe Val Leu Val Leu Ala Leu Leu His Ser His Leu Ala Ser Glu Met
                260                 265                 270

Phe Ala Ala Pro Met Gly Arg Cys Ala Ala Gly Val Met His Leu Phe
            275                 280                 285

Tyr Val Arg Ala Gly Val Ser Arg Ala Met Leu Leu Arg Leu Phe Leu
        290                 295                 300

Ala Met Glu Lys Gly Arg His Met Glu Tyr Glu Cys Pro Tyr Leu Val
305                 310                 315                 320

Tyr Val Pro Val Val Ala Phe Arg Leu Glu Pro Lys Asp Gly Lys Gly
                325                 330                 335

Val Phe Ala Val Asp Gly Glu Leu Met Val Ser Glu Ala Val Gln Gly
            340                 345                 350

Gln Val His Pro Asn Tyr Phe Trp Met Val Ser Gly Cys Val Glu Pro
        355                 360                 365

Pro Pro Ser Trp Lys Pro Gln Gln Met Pro Pro Glu Glu Pro Leu
    370                 375                 380

<210> SEQ ID NO 3
<211> LENGTH: 1759
<212> TYPE: DNA
<213> ORGANISM: Mus musculus

<400> SEQUENCE: 3
gaactccagg gtcctctggg agagaagcca ccttcaaggc gtgacctagt tcactgcaat     60
cctttcttat ctgggttcgt tttcctcttg gactcgcctc ttctggactt taagaagcga    120
tgcgaagata gagatctggc cgccccgggg aatgacgagg cgctcacac agcccaggga    180 ggtggagagg gcgagcccac ggccagtcgc cagacaccct cctgggcaac accgataaga    240
agctgaacgc aggagccgcc gttacctcta gcagcgccgg ggcagcaccg gtggcccctt    300
gtcagcggga gccccgggac ctggctatgg aaccagtaga atgccctcga ggactgctcc    360
cacggccatg cagagtgctg gtgctgctga ccccagggg tggcaagggc aaggctctgc    420
agctcttcca gagccgtgtg cagcccttcc tggaggagga agataacc tttaaactga    480 tactcaccga acggaagaac catgccaggg agctggtgtg tgcagaggag ttgggtcact    540
gggacgccct ggcagtcatg tccggtgatg gtctgatgca tgaagtggtg aatgggctaa    600
tggaacggcc agactgggag actgccatcc agaaacccct gtgtagcctc cctggaggct    660
ccggcaatgc gctggcagct tctgtgaacc actatgctgg gtacgagcag gtgactaatg    720
aagacctgct catcaactgc acactgctgt tgtgccgccg gcgcctgtca cccatgaacc    780
tgctgtccct gcacactgct tctgggctgc ggctctattc tgtgctcagt ctgtcctggg    840
gctttgttgc tgacgtggac ctcgagagtg agaagtacag gcgcttgggg gagattcgtt    900
```

-continued

```
tcacagtggg cacctcttt cgcctagcaa gcctgcgcat ctaccaaggc caactggcct      960
accttcctgt aggaactgtg gcctctaaga gacccgcctc tacactggtg cagaagggcc   1020
ccgtcgacac acaccttgtt cctctggagg agccagtgcc ttctcattgg actgtggtac   1080
cagaacagga cttcgtcctg gtgctggtgc tgctacacac ccacctgagc tccgagctgt   1140
ttgcagcacc catgggccgc tgtgaggctg gtgttatgca tctgttctac gtacgtgcgg   1200
gggtgtcaag ggctgcgctg ctgcgcctct tcctggccat gcagaagggc aagcatatgg   1260
aacttgactg tccatacctg gttcatgtgc ccgtggttgc tttccgcctg gagcccagga   1320
gccagagggg cgtgttttct gtggatggag agctgatggg atgtgaagct gtgcagggcc   1380
aagtgcaccc aaactacctt tggatggtct gtggcagcag agatgcccca tccggccggg   1440
actcccggcg ggggccacct ccagaagaac cataactctg tgcctttgtc tactctgtct   1500
aggctgagat gggaccctcc cccgcaccca cctcctggta tgggaggtta tttctaaagt   1560
tcctatggaa gtggtgggga ccctgcagaa gaaagctaga aggtggggct atgacttgga   1620
aagaaaggct ttaccttcca gttagagtaa catccccagt agagccctgc tggctggacc   1680
agttgcatat agaagacatt ccccattgct tttagggacc ttccctggga accaaattca   1740
aataaagaga cttttccaa                                                 1759
```

<210> SEQ ID NO 4
<211> LENGTH: 382
<212> TYPE: PRT
<213> ORGANISM: Mus musculus

<400> SEQUENCE: 4

```
Met Glu Pro Val Glu Cys Pro Arg Gly Leu Pro Arg Pro Cys Arg
  1               5                  10                  15

Val Leu Val Leu Leu Asn Pro Gln Gly Gly Lys Gly Lys Ala Leu Gln
                 20                  25                  30

Leu Phe Gln Ser Arg Val Gln Pro Phe Leu Glu Glu Ala Glu Ile Thr
             35                  40                  45

Phe Lys Leu Ile Leu Thr Glu Arg Lys Asn His Ala Arg Glu Leu Val
         50                  55                  60

Cys Ala Glu Glu Leu Gly His Trp Asp Ala Leu Ala Val Met Ser Gly
 65                  70                  75                  80

Asp Gly Leu Met His Glu Val Val Asn Gly Leu Met Glu Arg Pro Asp
                 85                  90                  95

Trp Glu Thr Ala Ile Gln Lys Pro Leu Cys Ser Leu Pro Gly Gly Ser
            100                 105                 110

Gly Asn Ala Leu Ala Ala Ser Val Asn His Tyr Ala Gly Tyr Glu Gln
        115                 120                 125

Val Thr Asn Glu Asp Leu Leu Ile Asn Cys Thr Leu Leu Leu Cys Arg
    130                 135                 140

Arg Arg Leu Ser Pro Met Asn Leu Leu Ser Leu His Thr Ala Ser Gly
145                 150                 155                 160

Leu Arg Leu Tyr Ser Val Leu Ser Leu Ser Trp Gly Phe Val Ala Asp
                165                 170                 175

Val Asp Leu Glu Ser Glu Lys Tyr Arg Arg Leu Gly Glu Ile Arg Phe
            180                 185                 190

Thr Val Gly Thr Phe Phe Arg Leu Ala Ser Leu Arg Ile Tyr Gln Gly
        195                 200                 205

Gln Leu Ala Tyr Leu Pro Val Gly Thr Val Ala Ser Lys Arg Pro Ala
    210                 215                 220
```

```
Ser Thr Leu Val Gln Lys Gly Pro Val Asp Thr His Leu Val Pro Leu
225                 230                 235                 240
Glu Glu Pro Val Pro Ser His Trp Thr Val Pro Glu Gln Asp Phe
            245                 250                 255
Val Leu Val Leu Val Leu Leu His Thr His Leu Ser Ser Glu Leu Phe
                260                 265                 270
Ala Ala Pro Met Gly Arg Cys Glu Ala Gly Val Met His Leu Phe Tyr
            275                 280                 285
Val Arg Ala Gly Val Ser Arg Ala Ala Leu Leu Arg Leu Phe Leu Ala
        290                 295                 300
Met Gln Lys Gly Lys His Met Glu Leu Asp Cys Pro Tyr Leu Val His
305                 310                 315                 320
Val Pro Val Val Ala Phe Arg Leu Glu Pro Arg Ser Gln Arg Gly Val
                325                 330                 335
Phe Ser Val Asp Gly Glu Leu Met Val Cys Glu Ala Val Gln Gly Gln
            340                 345                 350
Val His Pro Asn Tyr Leu Trp Met Val Cys Gly Ser Arg Asp Ala Pro
        355                 360                 365
Ser Gly Arg Asp Ser Arg Arg Gly Pro Pro Glu Glu Pro
        370                 375                 380

<210> SEQ ID NO 5
<211> LENGTH: 1840
<212> TYPE: DNA
<213> ORGANISM: Homo sapiens

<400> SEQUENCE: 5
gccggcgccc ccggcgcgga tgcctgctct gtgcctgtat ctgagatcat cgccgttgag      60
gaaacagacg ttcacgggaa acatcaaggc agtggaaaat ggcagaaaat ggaaaagcct     120
tacgctttta cagttcactg tgtaaagaga gcacgacggc accgctggaa gtgggcgcag     180
gtgactttct ggtgtccaga ggagcagctg tgtcacttgt ggctgcagac cctgcgggag     240
atgctggaga agctgacgtc cagaccaaag catttactgg tatttatcaa cccgtttgga     300
ggaaaaggac aaggcaagcg atatatgaa agaaaagtgg caccactgtt caccttagcc     360
tccatcacca ctgacatcat cggtaacaaa ttctatgtta actatgtaga agtaattact     420
gaacatgcta atcaggccaa ggagactctg tatgagatta catagacaa atacgacggc     480 atcgtctgtg tcggcggaga tggtatgttc agcgaggtgc tgcacggtct gattgggagg     540
acgcagagga gcgccggggt cgaccagaac caccccgggg ctgtgctggt ccccagtagc     600
ctccggattg gaatcattcc cgcagggtca acggactgcg tgtgttactc caccgtgggc     660
accagcgacg cagaaacctc ggcgctgcat atcgttgttg gggactcgct ggccatggat     720
gtgtcctcag tccaccacaa cagcacactc cttcgctact ccgtgtccct gctgggctac     780
ggcttctacg gggacatcat caaggacagt gagaagaaac ggtggttggg tcttgccaga     840
tacgactttt caggtttaaa gaccttcctc tccaccact gctatgaagg acagtgtcc     900 ttcctccctg cacaacacac ggtgggatct ccaagggata ggaagccctg ccgggcagga     960
tgctttgttt gcaggcaaag caagcagcag ctggaggagg agcagaagaa agcactgtat    1020
ggtttggaag ctgcggagga cgtggaggag tggcaagtcg tctgtgggaa gtttctggcc    1080
atcaatgcca caaacatgtc ctgtgcttgt cgccggagcc caggggcct ctccccggct    1140 gcccacttgg gagacgggtc ttctgacctc atcctcatcc ggaaatgctc caggttcaat    1200
tttctgagat ttctcatcag gcacaccaac cagcaggacc agtttgactt cacttttgtt    1260
```

```
gaagtttatc gcgtcaagaa attccagttt acgtcgaagc acatggagga tgaggacagc    1320
gacctcaagg agggggggaa gaagcgcttt gggcacattt gcagcagcca cccctcctgc    1380
tgctgcaccg tctccaacag ctcctggaac tgcgacgggg aggtcctgca cagccctgcc    1440
atcgaggtca ggtccactg ccagctggtt cgactctttg cacgaggaat tgaagagaat    1500
ccgaagccag actcacacag ctgagaagcc ggcgtcctgc tcacaaactg ggaaagtgtg    1560
aaaactattt aagataatta ttacagacca attatgttga tatatacatt taaatgtaga    1620
aatttatttt tgatagttaa atcttgattt tagaagaaaa ccctttttgtc aacaattttg    1680 tgtacatatt tggcattttc agttctgtac gcatctgcgg gttgcagccc acgccgctta    1740
ctctcagcaa gaaagaggtg gaggttgcgg tgagccaaga ttgcgccact gcactccagc    1800
ctgggcaaac agaggagac tccatcgccc cccccaacaa                           1840
```

<210> SEQ ID NO 6
<211> LENGTH: 471
<212> TYPE: PRT
<213> ORGANISM: Homo sapiens

<400> SEQUENCE: 6

```
Met Glu Lys Pro Tyr Ala Phe Thr Val His Cys Val Lys Arg Ala Arg
  1               5                  10                  15

Arg His Arg Trp Lys Trp Ala Gln Val Thr Phe Trp Cys Pro Glu Glu
                 20                  25                  30

Gln Leu Cys His Leu Trp Leu Gln Thr Leu Arg Glu Met Leu Glu Lys
             35                  40                  45

Leu Thr Ser Arg Pro Lys His Leu Leu Val Phe Ile Asn Pro Phe Gly
 50                  55                  60

Gly Lys Gly Gln Gly Lys Arg Ile Tyr Glu Arg Lys Val Ala Pro Leu
 65                  70                  75                  80

Phe Thr Leu Ala Ser Ile Thr Thr Asp Ile Ile Gly Asn Lys Phe Tyr
                 85                  90                  95

Val Asn Tyr Val Glu Val Ile Thr Glu His Ala Asn Gln Ala Lys Glu
                100                 105                 110

Thr Leu Tyr Glu Ile Asn Ile Asp Lys Tyr Asp Gly Ile Val Cys Val
            115                 120                 125

Gly Gly Asp Gly Met Phe Ser Glu Val Leu His Gly Leu Ile Gly Arg
130                 135                 140

Thr Gln Arg Ser Ala Gly Val Asp Gln Asn His Pro Arg Ala Val Leu
145                 150                 155                 160

Val Pro Ser Ser Leu Arg Ile Gly Ile Ile Pro Ala Gly Ser Thr Asp
                165                 170                 175

Cys Val Cys Tyr Ser Thr Val Gly Thr Ser Asp Ala Glu Thr Ser Ala
                180                 185                 190

Leu His Ile Val Val Gly Asp Ser Leu Ala Met Asp Val Ser Ser Val
            195                 200                 205

His His Asn Ser Thr Leu Leu Arg Tyr Ser Val Ser Leu Leu Gly Tyr
210                 215                 220

Gly Phe Tyr Gly Asp Ile Ile Lys Asp Ser Glu Lys Lys Arg Trp Leu
225                 230                 235                 240

Gly Leu Ala Arg Tyr Asp Phe Ser Gly Leu Lys Thr Phe Leu Ser His
                245                 250                 255

His Cys Tyr Glu Gly Thr Val Ser Phe Leu Pro Ala Gln His Thr Val
                260                 265                 270
```

```
Gly Ser Pro Arg Asp Arg Lys Pro Cys Arg Ala Gly Cys Phe Val Cys
        275                 280                 285

Arg Gln Ser Lys Gln Gln Leu Glu Glu Gln Lys Lys Ala Leu Tyr
        290                 295                 300

Gly Leu Glu Ala Ala Glu Asp Val Glu Glu Trp Gln Val Val Cys Gly
305                 310                 315                 320

Lys Phe Leu Ala Ile Asn Ala Thr Asn Met Ser Cys Ala Cys Arg Arg
                325                 330                 335

Ser Pro Arg Gly Leu Ser Pro Ala Ala His Leu Gly Asp Gly Ser Ser
            340                 345                 350

Asp Leu Ile Leu Ile Arg Lys Cys Ser Arg Phe Asn Phe Leu Arg Phe
            355                 360                 365

Leu Ile Arg His Thr Asn Gln Gln Asp Gln Phe Asp Phe Thr Phe Val
370                 375                 380

Glu Val Tyr Arg Val Lys Lys Phe Gln Phe Thr Ser Lys His Met Glu
385                 390                 395                 400

Asp Glu Asp Ser Asp Leu Lys Glu Gly Gly Lys Lys Arg Phe Gly His
                405                 410                 415

Ile Cys Ser Ser His Pro Ser Cys Cys Cys Thr Val Ser Asn Ser Ser
                420                 425                 430

Trp Asn Cys Asp Gly Glu Val Leu His Ser Pro Ala Ile Glu Val Arg
            435                 440                 445

Val His Cys Gln Leu Val Arg Leu Phe Ala Arg Gly Ile Glu Glu Asn
        450                 455                 460

Pro Lys Pro Asp Ser His Ser
465                 470

<210> SEQ ID NO 7
<211> LENGTH: 522
<212> TYPE: DNA
<213> ORGANISM: Rattus sp.

<400> SEQUENCE: 7
gtggatatgt caacataatt ggtcagtcga aattttctta agtaatattc acacttccca      60
aagctcctgg gctttgggat tcttccttag gactcttctt cgatcccccg agcaaagagg     120
cgcaccagct ggcagtggac cctgacctca atggcagggc tgtgcaggac ttccccatca     180
cagttccagg agcttctaga ggttgggcag gcgcaagggg ggttgtcctt gcagatctgc     240
ccaaacttct gcttctctag ttccttcaag tcattgtcat catcttccac gtgctttgat     300
gtgaactgga atttcttgac tcgataaact tcaacgaaag tgaagccaaa ctgatcctcc     360
tggttggtgt gccggatgag gaatctcagg aagttgaacc tggagcattt ccggataagg     420
atgaggtcag aagacccatc tcccagatgg gcaaatgggg acaggccccc agggctccgg     480
ggacaagcac aggacatgtt ggtggagttg atagccagga ac                       522

<210> SEQ ID NO 8
<211> LENGTH: 144
<212> TYPE: PRT
<213> ORGANISM: Rattus sp.

<400> SEQUENCE: 8

Phe Leu Ala Ile Asn Ser Thr Asn Met Ser Cys Ala Cys Pro Arg Ser
  1               5                  10                  15

Pro Gly Gly Leu Ser Pro Phe Ala His Leu Gly Asp Gly Ser Ser Asp
             20                  25                  30
```

Leu Ile Leu Ile Arg Lys Cys Ser Arg Phe Asn Phe Leu Arg Phe Leu
             35                  40                  45

Ile Arg His Thr Asn Gln Glu Asp Gln Phe Gly Phe Thr Phe Val Glu
     50                  55                  60

Val Tyr Arg Val Lys Lys Phe Gln Phe Thr Ser Lys His Val Glu Asp
 65                  70                  75                  80

Asp Asp Asn Asp Leu Lys Glu Leu Glu Lys Gln Lys Phe Gly Gln Ile
                 85                  90                  95

Cys Lys Asp Asn Pro Pro Cys Ala Cys Pro Thr Ser Arg Ser Ser Trp
            100                 105                 110

Asn Cys Asp Gly Glu Val Leu His Ser Pro Ala Ile Glu Val Arg Val
        115                 120                 125

His Cys Gln Leu Val Arg Leu Phe Ala Arg Gly Ile Glu Glu Glu Ser
    130                 135                 140

<210> SEQ ID NO 9
<211> LENGTH: 382
<212> TYPE: DNA
<213> ORGANISM: Mus musculus

<400> SEQUENCE: 9
tttatcgagt caagaaattc cacttcacgt cgaagcacgt ggaagacgag gacaatgact    60
cgaaggaaca agagaagcag aagtttggga agatctgcaa ggacagaccc tcttgcactt   120
gctcagcctc cagaagctcc tggaactgcg atggcgaagt catgcacagc ccggccattg   180
aggtcagggt ccactgccag ctggtgcgcc tctttgctcg gggaatcgag gaagagtcat   240
aagcaagaac cccaaagccc aggagctgtc ggccttgagc tcggggagtg tggaaattac   300
ttaagaaaaa ttcgacagac cagttatgtt gatatatcca tttgaattta gaatttatt   360 tttgataggt aaatcttggt tt                                            382

<210> SEQ ID NO 10
<211> LENGTH: 79
<212> TYPE: PRT
<213> ORGANISM: Mus musculus

<400> SEQUENCE: 10

Tyr Arg Val Lys Lys Phe His Phe Thr Ser Lys His Val Glu Asp Glu
  1               5                  10                  15

Asp Asn Asp Ser Lys Glu Gln Glu Lys Gln Lys Phe Gly Lys Ile Cys
             20                  25                  30

Lys Asp Arg Pro Ser Cys Thr Cys Ser Ala Ser Arg Ser Ser Trp Asn
         35                  40                  45

Cys Asp Gly Glu Val Met His Ser Pro Ala Ile Glu Val Arg Val His
     50                  55                  60

Cys Gln Leu Val Arg Leu Phe Ala Arg Gly Ile Glu Glu Glu Ser
 65                  70                  75

<210> SEQ ID NO 11
<211> LENGTH: 326
<212> TYPE: PRT
<213> ORGANISM: Homo sapiens

<400> SEQUENCE: 11

Pro Lys His Leu Leu Val Phe Ile Asn Pro Phe Gly Gly Lys Gly Gln
  1               5                  10                  15

Gly Lys Arg Ile Tyr Glu Arg Lys Val Ala Pro Leu Phe Thr Leu Ala
             20                  25                  30

```
Ser Ile Thr Thr Asp Ile Ile Gly Asn Lys Phe Tyr Val Asn Tyr Val
        35                  40                  45

Glu Val Ile Thr Glu His Ala Asn Gln Ala Lys Glu Thr Leu Tyr Glu
 50                  55                  60

Ile Asn Ile Asp Lys Tyr Asp Gly Ile Val Cys Val Gly Gly Asp Gly
 65                  70                  75                  80

Met Phe Ser Glu Val Leu His Gly Leu Ile Gly Arg Thr Gln Arg Ser
                 85                  90                  95

Ala Gly Val Asp Gln Asn His Pro Arg Ala Val Leu Val Pro Ser Ser
                100                 105                 110

Leu Arg Ile Gly Ile Ile Pro Ala Gly Ser Thr Asp Cys Val Cys Tyr
            115                 120                 125

Ser Thr Val Gly Thr Ser Asp Ala Glu Thr Ser Ala Leu His Ile Val
        130                 135                 140

Val Gly Asp Ser Leu Ala Met Asp Val Ser Ser Val His His Asn Ser
145                 150                 155                 160

Thr Leu Leu Arg Tyr Ser Val Ser Leu Leu Gly Tyr Gly Phe Tyr Gly
                165                 170                 175

Asp Ile Ile Lys Asp Ser Glu Lys Lys Arg Trp Leu Gly Leu Ala Arg
                180                 185                 190

Tyr Asp Phe Ser Gly Leu Lys Thr Phe Leu Ser His His Cys Tyr Glu
            195                 200                 205

Gly Thr Val Ser Phe Leu Pro Ala Gln His Thr Val Gly Ser Pro Arg
        210                 215                 220

Asp Arg Lys Pro Cys Arg Ala Gly Cys Phe Val Cys Arg Gln Ser Lys
225                 230                 235                 240

Gln Gln Leu Glu Glu Glu Gln Lys Lys Ala Leu Tyr Gly Leu Glu Ala
                245                 250                 255

Ala Glu Asp Val Glu Glu Trp Gln Val Val Cys Gly Lys Phe Leu Ala
                260                 265                 270

Ile Asn Ala Thr Asn Met Ser Cys Ala Cys Arg Arg Ser Pro Arg Gly
            275                 280                 285

Leu Ser Pro Ala Ala His Leu Gly Asp Gly Ser Ser Asp Leu Ile Leu
        290                 295                 300

Ile Arg Lys Cys Ser Arg Phe Asn Phe Leu Arg Phe Leu Ile Arg His
305                 310                 315                 320

Thr Asn Gln Gln Asp Gln
                325

<210> SEQ ID NO 12
<211> LENGTH: 453
<212> TYPE: PRT
<213> ORGANISM: Saccharomyces cerevisiae

<400> SEQUENCE: 12

Leu Tyr Ile Asp Tyr Lys Pro His Ser Ser His Leu Lys Glu Glu
  1               5                  10                  15

Asp Asp Leu Val Glu Glu Ile Leu Lys Arg Ser Tyr Lys Asn Thr Arg
             20                  25                  30

Arg Asn Lys Ser Ile Phe Val Ile Asn Pro Phe Gly Gly Lys Gly
             35                  40                  45

Lys Ala Lys Lys Leu Phe Met Thr Lys Ala Lys Pro Leu Leu Leu Ala
 50                  55                  60

Ser Arg Cys Ser Ile Glu Val Val Tyr Thr Lys Tyr Pro Gly His Ala
 65                  70                  75                  80
```

```
Ile Glu Ile Ala Arg Glu Met Asp Ile Asp Lys Tyr Asp Thr Ile Ala
                85                  90                  95

Cys Ala Ser Gly Asp Gly Ile Pro His Glu Val Ile Asn Gly Leu Tyr
            100                 105                 110

Gln Arg Pro Asp His Val Lys Ala Phe Asn Asn Ile Ala Ile Thr Glu
        115                 120                 125

Ile Pro Cys Gly Ser Gly Asn Ala Met Ser Val Ser Cys His Trp Thr
    130                 135                 140

Asn Asn Pro Ser Tyr Ser Thr Leu Cys Leu Ile Lys Ser Ile Glu Thr
145                 150                 155                 160

Arg Ile Asp Leu Met Cys Cys Ser Gln Pro Ser Tyr Ala Arg Glu His
                165                 170                 175

Pro Lys Leu Ser Phe Leu Ser Gln Thr Tyr Gly Leu Ile Ala Glu Thr
            180                 185                 190

Asp Ile Asn Thr Glu Phe Ile Arg Trp Met Gly Pro Ala Arg Phe Glu
        195                 200                 205

Leu Gly Val Ala Phe Asn Ile Ile Gln Lys Lys Tyr Pro Cys Glu
    210                 215                 220

Ile Tyr Val Lys Tyr Ala Ala Lys Ser Lys Asn Glu Leu Lys Asn His
225                 230                 235                 240

Tyr Leu Glu His Lys Asn Lys Gly Ser Leu Glu Phe Gln His Ile Thr
                245                 250                 255

Met Asn Lys Asp Asn Glu Asp Cys Asp Asn Tyr Asn Tyr Glu Asn Glu
            260                 265                 270

Tyr Glu Thr Glu Asn Glu Asp Glu Asp Ala Asp Ala Asp Asp
        275                 280                 285

Glu Asp Ser His Leu Ile Ser Arg Asp Leu Ala Asp Ser Ser Ala Asp
    290                 295                 300

Gln Ile Lys Glu Glu Asp Phe Lys Ile Lys Tyr Pro Leu Asp Glu Gly
305                 310                 315                 320

Ile Pro Ser Asp Trp Glu Arg Leu Asp Pro Asn Ile Ser Asn Asn Leu
                325                 330                 335

Gly Ile Phe Tyr Thr Gly Lys Met Pro Tyr Val Ala Ala Asp Thr Lys
            340                 345                 350

Phe Phe Pro Ala Ala Leu Pro Ser Asp Gly Thr Met Asp Met Val Ile
        355                 360                 365

Thr Asp Ala Arg Thr Ser Leu Thr Arg Met Ala Pro Ile Leu Leu Gly
    370                 375                 380

Leu Asp Lys Gly Ser His Val Leu Gln Pro Glu Val Leu His Ser Lys
385                 390                 395                 400

Ile Leu Ala Tyr Lys Ile Pro Lys Leu Gly Asn Gly Leu Phe Ser
                405                 410                 415

Val Asp Gly Glu Lys Phe Pro Leu Glu Pro Leu Gln Val Glu Ile Met
            420                 425                 430

Pro Arg Leu Cys Lys Thr Leu Leu Arg Asn Gly Arg Tyr Val Asp Thr
        435                 440                 445

Asp Phe Asp Ser Met
    450

<210> SEQ ID NO 13
<211> LENGTH: 436
<212> TYPE: PRT
<213> ORGANISM: Saccharomyces cerevisiae
```

<400> SEQUENCE: 13

```
Leu Leu Ile Asp His Val Ser Arg Lys Ser Arg Ala Asn Thr Gly Glu
 1               5                  10                  15

Glu Asn Ile Ser Ser Gly Thr Val Glu Glu Ile Leu Glu Lys Ser Tyr
            20                  25                  30

Glu Asn Ser Lys Arg Asn Arg Ser Ile Leu Val Ile Ile Asn Pro His
        35                  40                  45

Gly Gly Lys Gly Thr Ala Lys Asn Leu Phe Leu Thr Lys Ala Arg Pro
    50                  55                  60

Ile Leu Val Glu Ser Gly Cys Lys Ile Glu Ile Ala Tyr Thr Lys Tyr
65                  70                  75                  80

Ala Arg His Ala Ile Asp Ile Ala Lys Asp Leu Asp Ile Ser Lys Tyr
                85                  90                  95

Asp Thr Ile Ala Cys Ala Ser Gly Asp Gly Ile Pro Tyr Glu Val Ile
            100                 105                 110

Asn Gly Leu Tyr Arg Arg Pro Asp Arg Val Asp Ala Phe Asn Lys Leu
        115                 120                 125

Ala Val Thr Gln Leu Pro Cys Gly Ser Gly Asn Ala Met Ser Ile Ser
    130                 135                 140

Cys His Trp Thr Asn Asn Pro Ser Tyr Ala Ala Leu Cys Leu Val Lys
145                 150                 155                 160

Ser Ile Glu Thr Arg Ile Asp Leu Met Cys Cys Ser Gln Pro Ser Tyr
                165                 170                 175

Met Asn Glu Trp Pro Arg Leu Ser Phe Leu Ser Gln Thr Tyr Gly Val
            180                 185                 190

Ile Ala Glu Ser Asp Ile Asn Thr Glu Phe Ile Arg Trp Met Gly Pro
        195                 200                 205

Val Arg Phe Asn Leu Gly Val Ala Phe Asn Ile Ile Gln Gly Lys Lys
    210                 215                 220

Tyr Pro Cys Glu Val Phe Val Lys Tyr Ala Ala Lys Ser Lys Lys Glu
225                 230                 235                 240

Leu Lys Val His Phe Leu Glu Asn Lys Asp Lys Asn Lys Gly Cys Leu
                245                 250                 255

Thr Phe Glu Pro Asn Pro Ser Pro Asn Ser Ser Pro Asp Leu Leu Ser
            260                 265                 270

Lys Asn Asn Ile Asn Asn Ser Thr Lys Asp Glu Leu Ser Pro Asn Phe
        275                 280                 285

Leu Asn Glu Asp Asn Phe Lys Leu Lys Tyr Pro Met Thr Glu Pro Val
    290                 295                 300

Pro Arg Asp Trp Glu Lys Met Asp Ser Glu Leu Thr Asp Asn Leu Thr
305                 310                 315                 320

Ile Phe Tyr Thr Gly Lys Met Pro Tyr Ile Ala Lys Asp Thr Lys Phe
                325                 330                 335

Phe Pro Ala Ala Leu Pro Ala Asp Gly Thr Ile Asp Leu Val Ile Thr
            340                 345                 350

Asp Ala Arg Ile Pro Val Thr Arg Met Thr Pro Ile Leu Leu Ser Leu
        355                 360                 365

Asp Lys Gly Ser His Val Leu Glu Pro Glu Val Ile His Ser Lys Ile
    370                 375                 380

Leu Ala Tyr Lys Ile Ile Pro Lys Val Glu Ser Gly Leu Phe Ser Val
385                 390                 395                 400

Asp Gly Glu Lys Phe Pro Leu Glu Pro Leu Gln Val Glu Ile Met Pro
                405                 410                 415
```

-continued

Met Leu Cys Lys Thr Leu Leu Arg Asn Gly Arg Tyr Ile Asp Thr Glu
            420                 425                 430
Phe Glu Ser Met
        435

<210> SEQ ID NO 14
<211> LENGTH: 380
<212> TYPE: PRT
<213> ORGANISM: Schizosaccharomyces pombe

<400> SEQUENCE: 14

Cys Trp Val Asp Phe Val Glu Asn Ser Asp Gln Phe Cys Glu Tyr Leu
  1               5                  10                  15

Leu Asp Val Ala Tyr Lys Gly Ile Lys Arg Ser Arg Arg Phe Ile Val
             20                  25                  30

Phe Ile Asn Pro His Gly Gly Lys Gly Lys Ala Lys His Ile Trp Glu
         35                  40                  45

Ser Glu Ala Glu Pro Val Phe Ser Ser Ala His Ser Ile Cys Glu Val
 50                  55                  60

Val Leu Thr Arg Arg Lys Asp His Ala Lys Ser Ile Ala Lys Asn Leu
 65                  70                  75                  80

Asp Val Gly Ser Tyr Asp Gly Ile Leu Ser Val Gly Gly Asp Gly Leu
                 85                  90                  95

Phe His Glu Val Ile Asn Gly Leu Gly Glu Arg Asp Asp Tyr Leu Glu
            100                 105                 110

Ala Phe Lys Leu Pro Val Cys Met Ile Pro Gly Gly Ser Gly Asn Ala
        115                 120                 125

Phe Ser Tyr Asn Ala Thr Gly Gln Leu Lys Pro Ala Leu Thr Ala Leu
130                 135                 140

Glu Ile Leu Lys Gly Arg Pro Thr Ser Phe Asp Leu Met Thr Phe Glu
145                 150                 155                 160

Gln Lys Gly Lys Lys Ala Tyr Ser Phe Leu Thr Ala Asn Tyr Gly Ile
                165                 170                 175

Ile Ala Asp Cys Asp Ile Gly Thr Glu Asn Trp Arg Phe Met Gly Glu
            180                 185                 190

Asn Arg Ala Tyr Leu Gly Phe Phe Leu Arg Leu Phe Gln Lys Pro Asp
        195                 200                 205

Trp Lys Cys Ser Ile Glu Met Asp Val Val Ser Ser Asp Arg Thr Glu
210                 215                 220

Ile Lys His Met Tyr Glu Lys Ser Lys Asn Leu Ala Pro Met Ser Glu
225                 230                 235                 240

Ser Ser Asp Ser Asp Lys Thr Val Ser Thr Ser Pro Glu Ser His Leu
                245                 250                 255

Leu Thr Phe Glu Ile Asn Asp Leu Ser Ile Phe Cys Ala Gly Leu Leu
            260                 265                 270

Pro Tyr Ile Ala Pro Asp Ala Lys Met Phe Pro Ala Ala Ser Asn Asp
        275                 280                 285

Asp Gly Leu Ile Asp Val Val Ile Val Tyr Ser Lys Gln Phe Arg Lys
290                 295                 300

Ser Leu Leu Ser Met Phe Thr Gln Leu Asp Asn Gly Gly Phe Tyr Tyr
305                 310                 315                 320

Ser Lys His Leu Asn Tyr Tyr Lys Val Arg Ser Phe Arg Phe Thr Pro
                325                 330                 335

Val Asn Thr Gly Lys Arg His Tyr Phe Ala Leu Asp Gly Glu Ser Tyr
            340                 345                 350

Pro Leu Glu Pro Phe Glu Cys Arg Val Ala Pro Lys Leu Gly Thr Thr
          355                 360                 365

Leu Ser Pro Val Ala Gly Phe Gln Leu Leu Asp Ile
370                 375                 380

<210> SEQ ID NO 15
<211> LENGTH: 415
<212> TYPE: PRT
<213> ORGANISM: Caenorhabditis elegans

<400> SEQUENCE: 15

Cys Arg Ser Asp Ala Glu Asn Glu Gln Leu Thr Ser Val Ile Leu
 1               5                  10                  15

Ser Arg Lys Pro Pro Gln Glu Gln Cys Arg Gly Asn Leu Leu Val
                20                  25                  30

Phe Ile Asn Pro Asn Ser Gly Thr Gly Lys Ser Leu Glu Thr Phe Ala
            35                  40                  45

Asn Thr Val Gly Pro Lys Leu Asp Lys Ser Leu Ile Arg Tyr Glu Val
    50                  55                  60

Val Val Thr Thr Gly Pro Asn His Ala Arg Asn Val Leu Met Thr Lys
65                  70                  75                  80

Ala Asp Leu Gly Lys Phe Asn Gly Val Leu Ile Leu Ser Gly Asp Gly
                85                  90                  95

Leu Val Phe Glu Ala Leu Asn Gly Ile Leu Cys Arg Glu Asp Ala Phe
            100                 105                 110

Arg Ile Phe Pro Thr Leu Pro Ile Gly Ile Val Pro Ser Gly Ser Gly
            115                 120                 125

Asn Gly Leu Leu Cys Ser Val Leu Ser Lys Tyr Gly Thr Lys Met Asn
130                 135                 140

Glu Lys Ser Val Met Glu Arg Ala Leu Glu Ile Ala Thr Ser Pro Thr
145                 150                 155                 160

Ala Lys Ala Glu Ser Val Ala Leu Tyr Ser Val Lys Thr Asp Asn Gln
                165                 170                 175

Ser Tyr Ala Ser Phe Leu Ser Ile Gly Trp Gly Leu Met Ala Asp Ile
            180                 185                 190

Asp Ile Asp Ser Glu Lys Trp Arg Lys Ser Leu Gly His His Arg Phe
            195                 200                 205

Thr Val Met Gly Phe Ile Arg Ser Cys Asn Leu Arg Ser Tyr Lys Gly
210                 215                 220

Arg Leu Thr Tyr Arg Pro Tyr Lys Pro Lys Gly Phe His Pro Ser Ser
225                 230                 235                 240

Asn Val Phe Ser Val Tyr Glu Lys Thr Thr Gln Gln Arg Ile Asp Asp
                245                 250                 255

Ser Lys Val Lys Thr Asn Gly Ser Val Ser Asp Ser Glu Glu Glu Thr
            260                 265                 270

Met Glu Thr Lys Phe Gln Asn Trp Thr Leu Pro Asp Ser Asp Glu Thr
            275                 280                 285

Leu Ala Val Gly Ser Ser Asp Leu Glu Glu Thr Val Val Ile Glu Asp
            290                 295                 300

Asn Phe Val Asn Ile Tyr Ala Val Thr Leu Ser His Ile Ala Ala Asp
305                 310                 315                 320

Gly Pro Phe Ala Pro Ser Ala Lys Leu Glu Asp Asn Arg Ile His Leu
                325                 330                 335

Ser Tyr Ile Leu Trp Lys Asp Ile Gly Thr Arg Val Asn Ile Ala Lys
            340                 345                 350

-continued

```
Tyr Leu Leu Ala Ile Glu His Glu Thr His Leu Asp Leu Pro Phe Val
            355                 360                 365
Lys His Val Glu Val Ser Ser Met Lys Leu Glu Val Ile Ser Glu Gly
    370                 375                 380
Ser His Val Val Leu Asp Gly Glu Val Val Asp Thr Lys Thr Ile Glu
385                 390                 395                 400
Val Ala Ser Thr Lys Asn His Ile Ser Val Phe Ser Ser Thr Ala
                405                 410                 415

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 16

Asn Glu Gln Lys
 1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 17

Asn His Gln Lys
 1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 18

Asn Asp Glu Gln
 1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 19

Gln His Arg Lys
 1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:
      Illustrative motif
```

```
<400> SEQUENCE: 20

Met Ile Leu Val
  1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 21

Met Ile Leu Phe
  1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 22

Ser Thr Asn Lys
  1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 23

Ser Thr Pro Ala
  1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 24

Ser Gly Asn Asp
  1

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 25

Ser Asn Asp Glu Gln Lys
  1               5
```

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 26

Asn Asp Glu Gln His Lys
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 27

Asn Glu Gln His Arg Lys
 1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 28

Val Leu Ile Met
 1

<210> SEQ ID NO 29
<211> LENGTH: 182
<212> TYPE: PRT
<213> ORGANISM: Unknown Organism
<220> FEATURE:
<223> OTHER INFORMATION: Description of Unknown Organism: 80432911

<400> SEQUENCE: 29

Ala Gly Ala Pro Gly Ala Asp Ala Cys Ser Val Pro Val Ser Glu Ile
 1               5                  10                  15

Ile Ala Val Glu Glu Thr Asp Val His Gly Lys His Gln Gly Ser Gly
                20                  25                  30

Lys Trp Gln Lys Met Glu Lys Pro Tyr Ala Phe Thr Val His Cys Val
            35                  40                  45

Lys Arg Ala Arg Arg His Arg Trp Lys Trp Ala Gln Val Thr Phe Trp
        50                  55                  60

Cys Pro Glu Glu Gln Leu Cys His Leu Trp Leu Gln Thr Leu Arg Glu
 65                  70                  75                  80

Met Leu Glu Lys Leu Thr Ser Arg Pro Lys His Leu Leu Val Phe Ile
                85                  90                  95

Asn Pro Phe Gly Gly Lys Gly Gln Gly Lys Arg Ile Tyr Glu Arg Lys
            100                 105                 110

Val Ala Pro Leu Phe Thr Leu Ala Ser Ile Thr Thr Asp Ile Ile Val
        115                 120                 125

Thr Glu His Ala Asn Gln Ala Lys Glu Thr Leu Tyr Glu Ile Asn Ile
    130                 135                 140

-continued

```
Asp Lys Tyr Asp Gly Ile Val Cys Val Gly Gly Asp Gly Met Phe Ser
145                 150                 155                 160

Glu Val Leu His Gly Leu Ile Gly Arg Thr Gln Arg Ser Ala Gly Val
                165                 170                 175

Asp Gln Asn His Pro Arg
            180
```

SPHINGOSINE KINASES

RELATED APPLICATIONS

This application claims priority to U.S. provisional applications Ser. No.60/182,360, filed Feb. 14, 2000, and Serial No. 60/191,261, filed Mar. 22, 2000, which are incorporated herein by reference in their entirety.

FIELD OF THE INVENTION

The invention generally relates to nucleic acids and polypeptides encoded therefrom. More specifically, the invention relates to nucleic acids encoding novel polypeptides, as well as vectors, host cells, antibodies, and recombinant methods for producing these nucleic acids and polypeptides. Particularly, the invention relates to novel proteins bearing sequence similarity to sphigosine kinases, nucleic acids that encode these proteins or fragments thereof, and antibodies that bind immunospecifically to such proteins.

BACKGROUND OF THE INVENTION

Sphingolipids serving as signaling molecules, have recently emerged as regulators of cell growth, differentiation, diverse cell phenotypes, and cell death. Signaling via sphingolipid turnover is exemplified by two distinct pathways: a) the formation of ceramide resulting from the activation of sphingomyelinase by TNF and a variety of other stimuli, and b) the formation of sphingosine-1-phosphate (S1P) upon activation of sphingosine kinase (SphK) by several growth factors such as platelet-derived growth factor and phorbol ester. Thus, it has been proposed that cells activate sphingomyelinase in response to cytokines, whereas growth factors activate SphK and thereby choose between the formation of ceramide that favors cell death versus S1P that inhibits death.

The importance of S1P and by consequence the importance of SphK is illustrated by a series of reports that showed their activity in endothelial cell survival and activation by cholesterol via the TNF pathway, in neutrophil activation, in transformed cell motility. ("Tumor necrosis factor-alpha-mediated signal transduction in human neutrophils: involvement of sphingomyelin metabolites in the priming effect of TNF-alpha on the fMLP-stimulated superoxide production." Niwa et al., *Life Sci* 2000;66(3):245–56; Overexpression of SphK inhibits chemotactic motility of several transformed cell lines independently of cell surface receptors acting via its substrate, sphingosine-1-phosphate. Wang et al., "Sphingosine-1-phosphate inhibits motility of human breast cancer cells independently of cell surface receptors."*Cancer Res* Dec. 15, 1999, 59(24):6185–91; "Activation of SphK by tumor necrosis factor-alpha inhibits apoptosis in human endothelial cells." Xia et al., *J Biol Chem* Nov. 26, 1999;274 (48):34499–505).

A mouse SphK is described in Kohama et al. ("Molecular cloning and functional characterization of murine SphK". *J Biol Chem.* Sep 11, 1998;273(37):23722–8). However, the authors did not have conclusive data on where the mouse protein starts, even if they showed that the mouse cDNAs they obtained have SphK activity in vivo. Furthermore, no human sequence has been deposited for this enzyme in GenBank or Geneseq. In their paper, Kohama et al. have an alignment that shows only a part of a hypothetical human sequence.

SUMMARY OF THE INVENTION

The inventor was able to obtain a full-length human sequence of an SphK with Kozak consensus. Analysis of the full-length human sequence allowed the elucidation of the start of the mouse protein. Furthermore, the inventor discovered a novel SphK that represents a new founder of a subfamily of SphKs.

The invention is based in part upon the discovery of novel nucleic acid sequences encoding novel polypeptides. Nucleic acids encoding the polypeptides disclosed in the invention, and derivatives and fragments thereof, will hereinafter be collectively designated as "SphK" nucleic acid or polypeptide sequences.

In one aspect, the invention provides an isolated SphK nucleic acid molecule encoding an SphK polypeptide that includes a nucleic acid sequence that has identity to the nucleic acid disclosed in SEQ ID NO:1, 3, 5, 7, or 9. In some embodiments, the SphK nucleic acid molecule can hybridize under stringent conditions to a nucleic acid sequence complementary to a nucleic acid molecule that includes a protein-coding sequence of an SphK nucleic acid sequence. The invention also includes an isolated nucleic acid that encodes an SphK polypeptide, or a fragment, homolog, analog or derivative thereof. For example, the nucleic acid can encode a polypeptide at least 80% identical to a polypeptide comprising the amino acid sequence of SEQ ID NO: 2, 4, 6, 8, 10, 12, 13, 14, or 15. The nucleic acid can be, for example, a genomic DNA fragment or a cDNA molecule that includes the nucleic acid sequence of any of SEQ ID NOS: 1, 3, 5, 7, and 9.

Also included in the invention is an oligonucleotide, e.g., an oligonucleotide that includes at least 6 contiguous nucleotides of an SphK nucleic acid (e.g., SEQ ID NO: 1, 3, 5, 7, or 9) or a complement of said oligonucleotide.

Also included in the invention are substantially purified SphK polypeptides (SEQ ID NO: 2, 4, 6, 8, 10, 12, 13, 14, or 15). In some embodiments, the SphK polypeptides include an amino acid sequence that is substantially identical to the amino acid sequence of a human SphK polypeptide.

The invention also features antibodies that immunoselectively-binds to SphK polypeptides.

In another aspect, the invention includes pharmaceutical compositions that include therapeutically- or prophylactically-effective amounts of a therapeutic and a pharmaceutically-acceptable carrier. The therapeutic can be, e.g., an SphK nucleic acid, an SphK polypeptide, or an antibody specific for an SphK polypeptide. In a further aspect, the invention includes, in one or more containers, a therapeutically- or prophylactically-effective amount of this pharmaceutical composition.

In a further aspect, the invention includes a method of producing a polypeptide by culturing a cell that includes an SphK nucleic acid, under conditions allowing for expression of the SphK polypeptide encoded by the DNA. If desired, the SphK polypeptide can then be recovered.

In another aspect, the invention includes a method of detecting the presence of an SphK polypeptide in a sample. In the method, a sample is contacted with a compound that selectively binds to the polypeptide under conditions allowing for formation of a complex between the polypeptide and the compound. The complex is detected, if present, thereby identifying the SphK polypeptide within the sample.

The invention also includes methods to identify specific cell or tissue types based on their expression of an SphK.

Also included in the invention is a method of detecting the presence of an SphK nucleic acid molecule in a sample by contacting the sample with an SphK nucleic acid probe or primer, and detecting whether the nucleic acid probe or primer bound to an SphK nucleic acid molecule in the sample.

In a further aspect, the invention provides a method for modulating the activity of an SphK polypeptide by contacting a cell sample that includes the SphK polypeptide with a compound that binds to the SphK polypeptide in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

Also within the scope of the invention is the use of a therapeutic in the manufacture of a medicament for treating or preventing disorders or syndromes including cell proliferative disorders, e.g., cancers, ischemia, or restenosis. The therapeutic can be, e.g. an SphK nucleic acid, an SphK polypeptide, or an SphK-specific antibody, or biologically-active derivatives or fragments thereof.

The invention further includes a method for screening for a modulator of disorders or syndromes including cell proliferative disorders, e.g., cancers, ischemia, or restenosis. The method includes contacting a test compound with an SphK polypeptide and determining if the test compound binds to said SphK polypeptide. Preferably, the effect of the contacting on enzymatic activity is determined. Compounds that affect SphK enzymatic activity may be modulators of disorders or syndromes.

Also within the scope of the invention is a method for screening for a modulator of activity, or of latency or predisposition to an disorders or syndromes including cell proliferative disorders, e.g., cancers, ischemia, or restenosis, by administering a test compound to a test animal at increased risk for the aforementioned disorders or syndromes. The test animal expresses a recombinant polypeptide encoded by an SphK nucleic acid. Expression or activity of SphK polypeptide is then measured in the test animal, as is expression or activity of the protein in a control animal which recombinantly-expresses SphK polypeptide and is not at increased risk for the disorder or syndrome. Next, the expression of SphK polypeptide in both the test animal and the control animal is compared. A change in the activity of SphK polypeptide in the test animal relative to the control animal indicates the test compound is a modulator of latency of the disorder or syndrome.

In yet another aspect, the invention includes a method for determining the presence of or predisposition to a disease associated with altered levels of an SphK polypeptide, an SphK nucleic acid, or both, in a subject (e.g., a human subject). The method includes measuring the amount of the SphK polypeptide in a test sample from the subject and comparing the amount of the polypeptide in the test sample to the amount of the SphK polypeptide present in a control sample. An alteration in the level of the SphK polypeptide in the test sample as compared to the control sample indicates the presence of or predisposition to a disease in the subject. Alternatively, rather than measuring the amount of SphK plypeptide, SphK enzymatic activity can be measured. Preferably, the predisposition includes cell proliferative disorders, e.g., cancers, ischemia, or restenosis. Also, the expression levels of the new polypeptides of the invention can be used in a method to screen for various cancers.

In a further aspect, the invention includes a method of treating or preventing a pathological condition associated with a disorder in a mammal by administering to the subject an SphK polypeptide, an SphK nucleic acid, or an SphK-specific antibody to a subject (e.g., a human subject), in an amount sufficient to alleviate or prevent the pathological condition. In preferred embodiments, the disorder includes cell proliferative disorders, e.g., cancers, ischemia, or restenosis.

In yet another aspect, the invention can be used in a method to identity the cellular receptors and downstream effectors of the invention by any one of a number of techniques commonly employed in the art. These include but are not limited to the two-hybrid system, affinity purification, co-precipitation with antibodies or other specific-interacting molecules.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIG. 1. Alignment of the novel human SphK (SPkinaseinHSDA59H18; SEQ ID NO: 6) with the amino acid sequence of CAB62977 (SEQ ID. NO: 11).

FIG. 2. Alignment of the novel human SphK (SPkinaseinHSDA59H18; SEQ ID NO: 6) with the rat (AI237625; SEQ ID NO: 8) and mouse (52180312; SEQ ID NO: 10) orthologs.

FIG. 3. Alignment of the novel human SphK (SPkinaseinHSDA59H18; SEQ ID NO: 6) with the human SphK of Example 1 (coorected_human_sphingosine; SEQ ID NO: 2), its mouse homolog (AF068748_EXT-2; SEQ ID NO: 4), along with homologs from other species (Q06147 (*Saccharomyces ceravisiae;* SEQ ID 0NO: 12); Q12246 (*Saccharomyces ceravisiae;* SEQ ID NO: 13); O14159 (*Schizosaccharomyces pombe;* SEQ ID NO: 14); and Q18425(*Caenorhabditis elegans;* SEQ ID NO: 15)).

FIG. 5. Alignment of SPkinaseinHSDA59H18 (SEQ ID NO: 6) and 80432911 (SEQ ID NO: 29).

Figure 4:
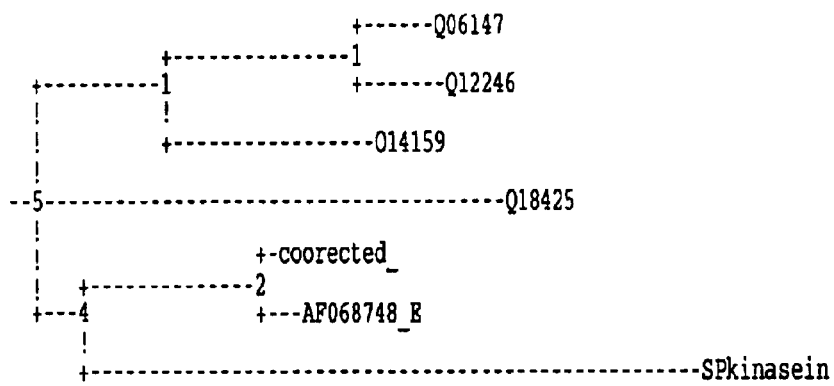
FIG. 4. Protein distance analysis of the SphKs.

Other features and advantages of the invention will be apparent from the following detailed description and claims.

DETAILED DESCRIPTION

The invention is based, in part, upon the discovery of novel nucleic acid sequences that encode novel polypeptides, particularly sphingosine kinases. The nucleic acids, and their encoded polypeptides, are collectively designated herein as "SphK".

The novel SphK nucleic acids of the invention include the nucleic acids whose sequences are provided as SEQ ID NO: 1, 3, 5, 7, or 9, or a fragment thereof. The invention also includes a mutant or variant SphK nucleic acid, any of whose bases may be changed from the corresponding base listed in SEQ ID NO: 1, 3, 5, 7, or 9 while still encoding a protein that maintains the activities and physiological functions of the SphK protein fragment, or a fragment of such a nucleic acid. The invention further includes nucleic acids whose sequences are complementary to those just described, including complementary nucleic acid fragments. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to 20% or more of the bases may be so changed.

The novel SphK proteins of the invention include the protein fragments whose sequences are provided as SEQ ID NO: 2, 4, 6, 8, 10, 12, 13, 14, or 15. The invention also includes an SphK mutant or variant protein, any of whose residues may be changed from the corresponding residue listed in SEQ ID NO: 2, 4, 6, 8, 10, 12, 13, 14, or 15 while still encoding a protein that maintains its native activities and physiological functions, or a functional fragment thereof. In the mutant or variant SphK protein, up to 20% or more of the residues may be so changed. The invention further encompasses antibodies and antibody fragments, such as $F_{ab}$ or $(F_{ab})_2$, that bind immunospecifically to any of the SphK proteins of the invention.

The SphK nucleic acids and proteins of the invention are useful in potential therapeutic applications implicated in various cancers, tumors and similar neoplastic diseases. For example, a cDNA encoding a polypeptide of SEQ ID NO: 2, 4, 6, 8, 10, 12, 13, 14, or 15 may be useful in gene therapy, and the polypeptide itself may be useful when administered to a subject in need thereof. The novel nucleic acids or polypeptides of the present, or fragments thereof, may further be useful in diagnostic applications, wherein the presence or amount of the nucleic acid or the protein are to be assessed. These materials are further useful in the generation of antibodies that bind immunospecifically to the novel substances of the invention for use in therapeutic or diagnostic methods.

SphK Nucleic Acids and Polypeptides

One aspect of the invention pertains to isolated nucleic acid molecules that encode SphK polypeptides or biologically-active portions thereof. Also included in the invention are nucleic acid fragments sufficient for use as hybridization probes to identify SphK-encoding nucleic acids (e.g., SphK mRNAs) and fragments for use as PCR primers for the amplification and/or mutation of SphK nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

An SphK nucleic acid can encode a mature SphK polypeptide. As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the fall length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "probes", as utilized herein, refers to nucleic acid sequences of variable length, preferably between at least about 10 nucleotides (nt), 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes may be single- or double-stranded and designed to have specificity in PCR, membrane-based hybridization technologies, array technologies, or ELISA-like technologies.

The term "isolated" nucleic acid molecule, as utilized herein, is one which is separated from other nucleic acid molecules which are present in the natural source of the nucleic acid. Preferably, an "isolated" nucleic acid is free of sequences that naturally flank the nucleic acid (i.e., sequences located at the 5'- and 3'-termini of the nucleic acid) in the genomic DNA of the organism from which the nucleic acid is derived. For example, in various embodiments, the isolated SphK nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a nucleic acid molecule having the nucleotide sequence of SEQ ID NO: 1, 3, 5, 7, or 9, or a complement of this aforementioned nucleotide sequence, can be isolated using standard molecular biology techniques and the sequence information provided herein. Using all or a portion of the nucleic acid sequence of SEQ ID NO: 1, 3, 5, 7, or 9 as a hybridization probe, SphK molecules can be isolated using standard hybridization and cloning techniques (e.g., as described in Sambrook, et al., (eds.), MOLECULAR CLONING: A LABORATORY MANUAL $2^{nd}$ Ed., Cold Spring Harbor Laboratory Press, Cold Spring Harbor, N.Y., 1989; and Ausubel, et al., (eds.), CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to SphK nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides of SEQ ID NO: 1, 3, 5, 7, or 9, or a complement thereof. Oligonucleotides may be chemically synthesized and may also be used as probes.

In another embodiment, an isolated nucleic acid molecule of the invention comprises a nucleic acid molecule that is a complement of the nucleotide sequence shown in SEQ ID NO: 1, 3, 5, 7, or 9, or a portion of this nucleotide sequence (e.g., a fragment that can be used as a probe or primer or a fragment encoding a biologically-active portion of an SphK polypeptide). A nucleic acid molecule that is complementary to the nucleotide sequence shown in SEQ ID NO:1, 3, 5, 7, or 9, is one that is sufficiently complementary to the nucleotide sequence shown in SEQ ID NO:1, 3, 5, 7, or 9, that it can hydrogen bond with little or no mismatches to the nucleotide sequence shown in SEQ ID NO:1, 3, 5, 7, or 9, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differ from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of SphK polypeptides. Isoforms can be expressed in different tissues of the same organism as a result of, for example, alternative splicing of RNA. Alternatively, isoforms may be encoded by different genes. In the invention, homologous nucleotide sequences include nucleotide sequences encoding for an SphK polypeptide of species other than humans, including, but not limited to: vertebrates, and thus can include, e.g., frog, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding human SphK protein. Homologous nucleic acid sequences include those nucleic acid sequences that encode conservative amino acid substitutions (see below) in SEQ ID NO:2, 4, 6, 8, 10, 12, 13, 14, or 15, as well as a polypeptide possessing SphK biological activity. Various biological activities of the SphK proteins are described below.

An SphK polypeptide is encoded by the open reading frame ("ORF") of an SphK nucleic acid. An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, e.g., a stretch of DNA that would encode a protein of 50 amino acids or more.

The nucleotide sequences determined from the SphK genes allows for the generation of probes and primers designed for use in identifying and/or cloning SphK homologues in other cell types, e.g. from other tissues, as well as SphK homologues from other vertebrates. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NO:1, 3, 5, 7, or 9; or an anti-sense strand nucleotide sequence of SEQ ID NO:1, 3, 5, 7, or 9; or of a naturally occurring mutant of SEQ ID NO:1, 3, 5, 7, or 9.

Probes based on the human SphK nucleotide sequences can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissues which mis-express an SphK protein, such as by measuring a level of an SphK-encoding nucleic acid in a sample of cells from a subject e.g., detecting SphK mRNA levels or determining whether a genomic SphK gene has been mutated or deleted.

"A polypeptide having a biologically-active portion of an SphK polypeptide" refers to polypeptides exhibiting activity similar, but not necessarily identical to, an activity of a polypeptide of the invention, including mature forms, as measured in a particular biological assay, with or without dose dependency. A nucleic acid fragment encoding a "biologically-active portion of SphK" can be prepared by isolating a portion of SEQ ID NO:1, 3, 5, 7, or 9, that encodes a polypeptide having an SphK biological activity (the biological activities of the SphK proteins are described below), expressing the encoded portion of SphK protein (e.g., by recombinant expression in vitro) and assessing the activity of the encoded portion of SphK.

SphK Nucleic Acid and Polypeptide Variants

The invention further encompasses nucleic acid molecules that differ from the nucleotide sequence shown in SEQ ID NO:1, 3, 5, 7, or 9, due to degeneracy of the genetic code and thus encode the same SphK protein as that encoded by the nucleotide sequence shown in SEQ ID NO:1, 3, 5, 7, or 9. In another embodiment, an isolated nucleic acid molecule of the invention has a nucleotide sequence encoding a protein having an amino acid sequence shown in SEQ ID NO:2, 4, 6, 8, 10, 12, 13, 14, or 15.

In addition to the SphK nucleotide sequences shown in SEQ ID NOS: 1, 3, 5, 7, and 9, it will be appreciated by those skilled in the art that DNA sequence polymorphisms that lead to changes in the amino acid sequences of the SphK polypeptides may exist within a population (e.g., the human population). Such genetic polymorphism in the SphK genes may exist among individuals within a population due to natural allelic variation. As used herein, the terms "gene" and "recombinant gene" refer to nucleic acid molecules comprising an open reading frame (ORF) encoding an SphK protein, preferably a vertebrate SphK protein. Such natural allelic variations can typically result in 1–5% variance in the nucleotide sequence of the SphK genes. Any and all such nucleotide variations and resulting amino acid polymorphisms in the SphK polypeptides, which are the result of natural allelic variation and that do not alter the functional activity of the SphK polypeptides, are intended to be within the scope of the invention.

Moreover, nucleic acid molecules encoding SphK proteins from additional species, and thus that have a nucleotide sequence that differs from the sequence of SEQ ID NO:1, 3, 5, 7, or 9, are intended to be within the scope of the invention. Nucleic acid molecules corresponding to natural allelic variants and homologues of the SphK cDNAs of the invention can be isolated based on their homology to the human SphK nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1, 3, 5, 7, or 9. In another embodiment, the nucleic acid is at least 10, 25, 50, 100, 250, 500, 750, 1000, 1500, or 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least 60% identical to each other typically remain hybridized to each other.

Homologs (i.e., nucleic acids encoding SphK proteins derived from species other than that from which the nucleic acid was originally isolated) or other related sequences (e.g., paralogs) can be obtained by low, moderate or high stringency hybridization with all or a portion of the particular sequence as a probe using methods well known in the art for nucleic acid hybridization and cloning.

As used herein, the phrase "stringent hybridization conditions" refers to conditions under which a probe, primer or oligonucleotide will hybridize to its target sequence, but preferably to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel, et al., (eds.), CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% identical to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequence SEQ ID NO:1, 3, 5, 7, or 9 may corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1, 3, 5, 7, or 9, or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel ,et al. (eds.), 1993, CURRENT PROTOCOLS IN MOLECULAR BIOLOGY, John Wiley & Sons, NY, and Kriegler, 1990; GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO:1, 3, 5, 7, or 9, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel, et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981. *Proc Natl Acad Sci USA* 78: 6789–6792.

Conservative Mutations

In addition to naturally-occurring allelic variants of SphK sequences that may exist in the population, the skilled artisan will further appreciate that changes can be introduced by mutation into the nucleotide sequence of SEQ ID NO:1, 3, 5, 7, or 9, thereby leading to changes in the amino acid sequences of the encoded SphK proteins, without altering the functional ability of said SphK proteins. For example, nucleotide substitutions leading to amino acid substitutions at "non-essential" amino acid residues can be made in the sequence of SEQ ID NO:2, 4, 6, 8, 10, 12, 13, 14, or 15. A "non-essential" amino acid residue is a residue that can be altered from the wild-type sequences of the SphK proteins without altering their biological activity, whereas an "essential" amino acid residue is required for such biological activity. For example, amino acid residues that are conserved among the SphK proteins of the invention are predicted to be particularly non-amenable to alteration. Amino acids for which conservative substitutions can be made are well-known within the art.

Another aspect of the invention pertains to nucleic acid molecules encoding SphK proteins that contain changes in amino acid residues that are not essential for activity. Such SphK proteins differ in amino acid sequence from SEQ ID NO:2, 4, 6, 8, 10, 12, 13, 14, or 15, yet retain biological activity. In one embodiment, the isolated nucleic acid molecule comprises a nucleotide sequence encoding a protein, wherein the protein comprises an amino acid sequence at least about 45% identical to the amino acid sequences of SEQ ID NO:2, 4, 6, 8, 10, 12, 13, 14, or 15. Preferably, the protein encoded by the nucleic acid molecule is at least about 60% identical to SEQ ID NO:2, 4, 6, 8, 10, 12, 13, 14, or 15; more preferably at least about 70% identical to SEQ ID NO:2, 4, 6, 8, 10, 12, 13, 14, or 15; still more preferably at least about 80% identical to SEQ ID NO:2, 4, 6, 8, 10, 12, 13, 14, or 15; even more preferably at least about 90% identical to SEQ ID NO:2, 4, 6, 8, 10, 12, 13, 14, or 15; and most preferably at least about 95% identical to SEQ ID NO:2, 4, 6, 8, 10, 12, 13, 14, or 15.

An isolated nucleic acid molecule encoding an SphK protein homologous to the protein of SEQ ID NOS:2, 4, 6, 8, 10, 12, 13, 14, or 15, can be created by introducing one or more nucleotide substitutions, additions or deletions into the nucleotide sequence of SEQ ID NO:1, 3, 5, 7, or 9, such that one or more amino acid substitutions, additions or deletions are introduced into the encoded protein.

Mutations can be introduced into SEQ ID NO:2, 4, 6, 8, 10, 12, 13, 14, or 15 by standard techniques, such as site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the SphK protein is replaced with another amino acid residue from the same side chain family. Alternatively, in another embodiment, mutations can be introduced randomly along all or part of an SphK coding sequence, such as by saturation mutagenesis, and the resultant mutants can be screened for SphK biological activity to identify mutants that retain activity. Following mutagenesis of SEQ ID NOS:1, 3, 5, 7, or 9, the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, (SEQ ID NO: 16), NHQK (SEQ ID NO: 17), NDEQ (SEQ ID NO: 18), QHRK (SEQ ID NO: 19), MILV (SEQ ID NO: 20), MILF (SEQ ID NO: 21), HY, FYW, wherein the single letter amino acid codes are grouped by those amino acids that may be substituted for each other. Likewise, the "weak" group of conserved residues may be any one of the following: CSA, ATV, SAG, STNK (SEQ ID NO: 22), STPA (SEQ ID NO: 23), SGND (SEQ ID NO: 24), SNDEQK (SEQ ID NO: 25), NDEQHK (SEQ ID NO: 26), NEQHRK (SEQ ID NO: 27), VLIM (SEQ ID NO: 28), HFY, wherein the letters within each group represent the single letter amino acid code.

In one embodiment, a mutant SphK protein can be assayed for kinase activity (e.g., the ability to convert sphingosine to sphingosine-1-P (S1P)). Methods of assaying SphK activity are known in the art (Banno et al., *Biochem J* Oct. 15, 1998;335 (Pt 2):301–4).

In yet another embodiment, a mutant SphK protein can be assayed for the ability to regulate a specific biological function (e.g., regulation of an S1P responsive signal transduction pathway).

Antisense Nucleic Acids

Another aspect of the invention pertains to isolated antisense nucleic acid molecules that are hybridizable to or complementary to the nucleic acid molecule comprising the nucleotide sequence of SEQ ID NO:1, 3, 5, 7, or 9, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire SphK coding strand, or to only a portion thereof. Nucleic acid molecules encoding fragments, homologs, derivatives and analogs of an SphK protein of SEQ ID NO:2, 4, 6, 8, 10, 12, 13, 14, or 15; or antisense nucleic acids complementary to an SphK nucleic acid sequence of SEQ ID NO:1, 3, 5, 7, or 9, are additionally provided.

In one embodiment, an antisense nucleic acid molecule is antisense to a "coding region" of the coding strand of a nucleotide sequence encoding an SphK protein. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding the SphK protein. The term "noncoding region" refers to 5' and 3' sequences that flank the coding region that are not translated into amino acids (ie., also referred to as 5' and 3' untranslated regions).

Given the coding strand sequences encoding the SphK proteins disclosed herein, antisense nucleic acids of the invention can be designed according to the rules of Watson and Crick or Hoogsteen base pairing. The antisense nucleic acid molecule can be complementary to the entire coding region of SphK mRNA, but more preferably is an oligonucleotide that is antisense to only a portion of the coding or noncoding region of SphK mRNA. For example, the antisense oligonucleotide can be complementary to the region surrounding the translation start site of SphK mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an SphK protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site by syringe, stent, or by catheter. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. See, e.g., Gaultier, et al., 1987. *Nucl. Acids Res.* 15: 6625–6641. The antisense nucleic acid molecule can also comprise a 2'-o-methylribonucleotide (see, e.g. Inoue, et al. 1987. *Nucl. Acids Res.* 15: 6131–6148) or a chimeric RNA-DNA analogue (see, e.g. Inoue, et al., 1987. *FEBS Lett.* 215:327–330.

Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585–591) can be used to catalytically cleave SphK mRNA transcripts to thereby inhibit translation of SphK mRNA. A ribozyme having specificity for an SphK-encoding nucleic acid can be designed based upon the nucleotide sequence of an SphK cDNA disclosed herein (i.e., SEQ ID NO:1, 3, 5, 7, or 9). For example, a derivative of a Tetrahymena L-19 IVS RNA can be constructed in which the nucleotide sequence of the active site is complementary to the nucleotide sequence to be cleaved in an SphK-encoding mRNA. See, e.g., U.S. Pat. No. 4,987,071 to Cech, et al. and U.S. Pat. No. 5,116,742 to Cech, et al. SphK mRNA can also be used to select a catalytic RNA having a specific ribonuclease activity from a pool of RNA molecules. See, e.g., Bartel et al., (1993) *Science* 261:1411–1418.

Alternatively, SphK gene expression can be inhibited by targeting nucleotide sequences complementary to the regulatory region of the SphK nucleic acid (e.g., the SphK promoter and/or enhancers) to form triple helical structures that prevent transcription of the SphK gene in target cells. See, e.g., Helene, 1991. *Anticancer Drug Des.* 6: 569–84; Helene, et al. 1992. *Ann. N.Y. Acad. Sci.* 660: 27–36; Maher, 1992. *Bioassays* 14: 807–15.

In various embodiments, the SphK nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. *Bioorg Med Chem* 4: 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. *Proc. Natl. Acad. Sci. USA* 93: 14670–14675.

PNAs of SphK can be used in therapeutic and diagnostic applications. For example, PNAs can be used as antisense or antigene agents for sequence-specific modulation of gene expression by, e.g., inducing transcription or translation arrest or inhibiting replication. PNAs of SphK can also be used, for example, in the analysis of single base pair mutations in a gene (e.g., PNA directed PCR clamping; as artificial restriction enzymes when used in combination with other enzymes, e.g., $S_1$ nucleases (see, Hyrup, et al., 1996.supra); or as probes or primers for DNA sequence and hybridization (see, Hyrup, et al., 1996, supra; Perry-O'Keefe, et al., 1996. supra).

In another embodiment, PNAs of SphK can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of SphK can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. *Nucl Acids Res* 24: 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. *Nucl Acid Res* 17: 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. *Bioorg. Med. Chem. Lett.* 5: 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. *Proc. Natl. Acad. Sci. U.S.A.* 86: 6553–6556; Lemaitre, et al., 1987. *Proc. Natl. Acad. Sci.* 84: 648–652; PCT Publication No. WO88/09810) or the blood-brain barrier (see, e.g., PCT Publication No. WO 89/10134). In addition, oligonucleotides can be modified with hybridization triggered cleavage agents (see, e.g., Krol, et al., 1988. *BioTechniques* 6:958–976) or intercalating agents (see, e.g., Zon, 1988. *Pharm. Res.* 5: 539–549). To this end, the oligonucleotide may be conjugated to another molecule, e.g., a peptide, a hybridization triggered cross-linking agent, a transport agent, a hybridization-triggered cleavage agent, and the like.

SphK Polypeptides

A polypeptide according to the invention includes a polypeptide including the amino acid sequence of SphK polypeptides whose sequences are provided in SEQ ID NOS: 2, 4, 6, 8, 10, 12, 13, 14, and 15. The invention also includes a mutant or variant protein any of whose residues may be changed from the corresponding residues shown in SEQ ID NO:2, 4, 6, 8, 10, 12, 13, 14, or 15, while still encoding a protein that maintains its SphK activities and physiological functions, or a functional fragment thereof.

In general, an SphK variant that preserves SphK-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated SphK proteins, and biologically-active portions thereof, or derivatives, fragments, analogs or homologs thereof. Also provided are polypeptide fragments suitable for use as immunogens to raise anti-SphK antibodies. In one embodiment, native SphK proteins can be isolated from cells or tissue sources by an appropriate purification scheme using standard protein purification techniques. In another embodiment, SphK proteins are produced by recombinant DNA techniques. Alternative to recombinant expression, an SphK protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the SphK protein is derived, or substantially free from chemical precursors or other chemicals when chemically synthesized. The language "substantially free of cellular material" includes preparations of SphK proteins in which the protein is separated from cellular components of the cells from which it is isolated or recombinantly-produced. In one embodiment, the language "substantially free of cellular material" includes preparations of SphK proteins having less than about 30% (by dry weight) of non-SphK proteins (also referred to herein as a "contaminating protein"), more preferably less than about 20% of nonSphK proteins, still more preferably less than about 10% of non-SphK proteins, and most preferably less than about 5% of non-SphK proteins. When the SphK protein or biologically-active portion thereof is recombinantly-produced, it is also preferably substantially free of culture medium, i.e., culture medium represents less than about 20%, more preferably less than about 10%, and most preferably less than about 5% of the volume of the SphK protein preparation.

The language "substantially free of chemical precursors or other chemicals" includes preparations of SphK proteins in which the protein is separated from chemical precursors or other chemicals that are involved in the synthesis of the protein. In one embodiment, the language "substantially free of chemical precursors or other chemicals" includes preparations of SphK proteins having less than about 30% (by dry weight) of chemical precursors or non-SphK chemicals, more preferably less than about 20% chemical precursors or non-SphK chemicals, still more preferably less than about 10% chemical precursors or non-SphK chemicals, and most preferably less than about 5% chemical precursors or non-SphK chemicals.

Biologically-active portions of SphK proteins include peptides comprising amino acid sequences sufficiently homologous to or derived from the amino acid sequences of the SphK proteins (e.g., the amino acid sequence shown in SEQ ID NO:2, 4, 6, 8, 10, 12, 13, 14, or 15) that include fewer amino acids than the full-length SphK proteins, and exhibit at least one activity of an SphK protein. Typically, biologically-active portions comprise a domain or motif with at least one activity of the SphK protein. A biologically-active portion of an SphK protein can be a polypeptide which is, for example, 10, 25, 50, 100 or more amino acid residues in length.

Moreover, other biologically-active portions, in which other regions of the protein are deleted, can be prepared by recombinant techniques and evaluated for one or more of the functional activities of a native SphK protein.

In an embodiment, the SphK protein has an amino acid sequence shown in SEQ ID NO:2, 4, 6, 8, 10, 12, 13, 14, or 15. In other embodiments, the SphK protein is substantially homologous to SEQ ID NO:2, 4, 6, 8, 10, 12, 13, 14, or 15, and retains the functional activity of the protein of SEQ ID NO:2, 4, 6, 8, 10, 12, 13, 14, or 15, yet differs in amino acid sequence due to natural allelic variation or mutagenesis, as described in detail, below. Accordingly, in another embodiment, the SphK protein is a protein that comprises an amino acid sequence at least about 45% homologous to the amino acid sequence of SEQ ID NO:2, 4, 6, 8, 10, 12, 13, 14, or 15, and retains the functional activity of the SphK proteins of SEQ ID NO:2, 4, 6, 8, 10, 12, 13, 14, or 15.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch, 1970. *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1, 3, 5, 7, or 9.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides SphK chimeric or fusion proteins. As used herein, an SphK "chimeric protein" or "fusion protein" comprises an SphK polypeptide operatively-linked to a non-SphK polypeptide. A "SphK polypeptide" refers to a polypeptide having an amino acid sequence corresponding to an SphK protein (SEQ ID NO:2, 4, 6, 8, 10, 12, 13, 14, or 15), whereas a "non-SphK polypeptide" refers to a polypeptide having an amino acid sequence corresponding to a protein that is not substantially homologous to the SphK protein, e.g., a protein that is different from the SphK protein and that is derived from the same or a different organism. Within an SphK fusion protein the SphK polypeptide can correspond to all or a portion of an SphK protein. In one embodiment, an SphK fusion protein comprises at least one biologically-active portion of an SphK protein. In another embodiment, an SphK fusion protein comprises at least two biologically-active portions of an SphK protein. In yet another embodiment, an SphK fusion protein comprises at least three biologically-active portions of an SphK protein. Within the fusion protein, the term "operatively-linked" is intended to indicate that the SphK polypeptide and the non-SphK polypeptide are fused in-frame with one another. The non-SphK polypeptide can be fused to the N-terminus or C-terminus of the SphK polypeptide.

In one embodiment, the fusion protein is a GST-SphK fusion protein in which the SphK sequences are fused to the C-terminus of the GST (glutathione S-transferase) sequences. Such fusion proteins can facilitate the purification of recombinant SphK polypeptides.

In another embodiment, the fusion protein is an SphK protein containing a heterologous signal sequence at its N-terminus. In certain host cells (e.g., mammalian host cells), expression and/or secretion of SphK can be increased through use of a heterologous signal sequence.

In yet another embodiment, the fusion protein is an SphK-immunoglobulin fusion protein in which the SphK sequences are fused to sequences derived from a member of the immunoglobulin protein family. The SphK-immunoglobulin fusion proteins can be used to affect the bioavailability of an SphK substrate. Inhibition of the SphK substrate/SphK interaction may be useful therapeutically for both the treatment of proliferative and differentiative disorders, as well as modulating (e.g. promoting or inhibiting) cell survival. Moreover, the SphK-immunoglobulin fusion proteins of the invention can be used as immunogens to produce anti-SphK antibodies in a subject, to purify SphK binding molecule, and in screening assays to identify molecules that inhibit the interaction of SphK with sphingosine or an SphK binding molecule.

An SphK chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). An SphK-encoding nucleic acid can be cloned into such an expression vector such that the fusion moiety is linked in-frame to the SphK protein.

SphK Agonists and Antagonists

The invention also pertains to variants of the SphK proteins that function as either SphK agonists (i.e., mimetics) or as SphK antagonists. Variants of the SphK protein can be generated by mutagenesis (e.g., discrete point mutation or truncation of the SphK protein). An agonist of the SphK protein can retain substantially the same, or a subset of, the biological activities of the naturally occurring form of the SphK protein. An antagonist of the SphK protein can inhibit one or more of the activities of the naturally occurring form of the SphK protein by, for example, competitively binding to a downstream or upstream member of a cellular signaling cascade which includes the SphK protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the SphK proteins.

Variants of the SphK proteins that function as either SphK agonists (i.e., mimetics) or as SphK antagonists can be identified by screening combinatorial libraries of mutants (e.g., truncation mutants) of the SphK proteins for SphK protein agonist or antagonist activity. In one embodiment, a variegated library of SphK variants is generated by combinatorial mutagenesis at the nucleic acid level and is encoded by a variegated gene library. A variegated library of SphK variants can be produced by, for example, enzymatically ligating a mixture of synthetic oligonucleotides into gene sequences such that a degenerate set of potential SphK sequences is expressible as individual polypeptides, or alternatively, as a set of larger fusion proteins (e.g., for phage display) containing the set of SphK sequences therein. There are a variety of methods that can be used to produce libraries of potential SphK variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential SphK sequences. Methods for synthesizing degenerate oligonucleotides are well-known within the art. See, e.g., Narang, 1983. *Tetrahedron* 39: 3; Itakura, et al., 1984. *Annu. Rev. Biochem.* 53: 323; Itakura, et al., 1984. *Science* 198: 1056; Ike, et al., 1983. *Nucl. Acids Res.* 11: 477.

Polypeptide Libraries

In addition, libraries of fragments of the SphK protein coding sequences can be used to generate a variegated population of SphK fragments for screening and subsequent selection of variants of an SphK protein. In one embodiment, a library of coding sequence fragments can be generated by treating a double stranded PCR fragment of an SphK coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encodes N-terminal and internal fragments of various sizes of the SphK proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of SphK proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify SphK variants. See, e.g. Arkin and Yourvan, 1992. *Proc. Natl. Acad. Sci. USA* 89: 7811–7815; Delgrave, et al., 1993. *Protein Engineering* 6:327–331.

Anti-SphK Antibodies

The invention encompasses antibodies and antibody fragments, such as $F_{ab}$ or $(F_{ab})_2$, that bind immunospecifically to any of the SphK polypeptides of said invention. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain. Reference herein to antibodies includes a reference to all such classes, subclasses and types of human antibody species.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:2, 4, 6, 8, 10, 12, 13, 14, or 15 and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of SphK that is located on the surface of the protein, e.g., a hydrophilic region. A hydrophobicity analysis of the SphK protein sequence will indicate which regions of a SphK polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each incorporated herein by reference in their entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

1. Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum,* or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen that is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia, Pa., Vol. 14, No. 8 (Apr. 17, 2000), pp. 25–28).

2. Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding,1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

3. Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

4. Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al, (*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals that are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

5. $F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

6. Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature,* 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.,* 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers that are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells that express a particular antigen. These antibodies possess an antigen-binding arm and an arm that binds a cytotoxic agent or a radionuclide chelator, such as EOTUBE, DPTA, DOTA, or TETA. Another bispecific antibody of interest binds the protein antigen described herein and further binds tissue factor (TF).

7. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

8. Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity can also be prepared using heterobifunctional cross-linkers as described in Wolff et al. *Cancer Research*, 53: 2560–2565 (1993). Alternatively, an antibody can be engineered that has dual Fc regions and can thereby have enhanced complement lysis and ADCC capabilities. See Stevenson et al., *Anti-Cancer Drug Design*, 3: 219–230 (1989).

9. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, 131I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

10. Immunoliposomes

The antibodies disclosed herein can also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al ., *J. Biol. Chem.*, 257: 286–288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

11. Diagnostic Applications of Antibodies Directed Against the Proteins of the Invention Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds (see below).

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

12. Antibody Therapeutics

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand that may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

13. Pharmaceutical Compositions of Antibodies

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889–7893 (1993). The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

14. ELISA Assay

An agent for detecting a SphK protein is an antibody capable of binding to the protein, preferably an antibody with a detectable label. Antibodies can be polyclonal, or more preferably, monoclonal. An intact antibody, or a fragment thereof (e.g., $F_{ab}$ or $F_{(ab)2}$) can be used. The term "labeled", with regard to the probe or antibody, is intended to encompass direct labeling of the probe or antibody by coupling (ie., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an SphK mRNA, protein, or genomic DNA in a biological sample in vitro as well as in vivo. For example, in vitro techniques for detection of an analyte mRNA include Northern hybridizations and in situ hybridizations. In vitro techniques for detection of SphK protein include enzyme linked immunosorbent assays (ELISAs), Western blots, immunoprecipitations, and immunofluorescence. In vitro techniques for detection of SphK genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Thory of Enzyme Immunoassays", P. Tijssen, Elsevier Science Publishers, Amsterdam, 1985. Furthermore, in vivo techniques for detection of SphK protein include introducing into a subject a labeled anti-SphK protein antibody. For example, the antibody can be labeled with a radioactive marker whose presence and location in a subject can be detected by standard imaging techniques.

SphK Recombinant Expression Vectors and Host Cells

Another aspect of the invention pertains to vectors, preferably expression vectors, containing a nucleic acid encoding an SphK protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention may be introduced into host cells to thereby produce proteins or peptides, including fusion proteins or peptides, encoded by nucleic acids as described herein (e.g., SphK proteins, mutant forms of SphK proteins, fusion proteins, etc.).

The recombinant expression vectors of the invention may be designed for expression of SphK proteins in prokaryotic or eukaryotic cells. For example, SphK proteins may be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the SphK expression vector is a yeast expression vector. Examples of vectors for expression in yeast *Saccharomyces cerivisae* include pYepSec1 (Baldari, et al., 1987. *EMBO J* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, SphK can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J* 8: 729–733) and immunoglobulins (Banerji, et al., 1983. *Cell* 33: 729–740; Queen and Baltimore, 1983. *Cell* 33: 741–748), neuron-specific promoters (e.g. the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to SphK mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constituitive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics.* Vol. 1(1)1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, SphK protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding SphK or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) SphK protein. Accordingly, the invention further provides methods for producing SphK protein using the host cells of the invention. In one embodiment, the method comprises culturing the host cell of invention (into which a recombinant expression vector encoding SphK protein has been introduced) in a suitable medium such that SphK protein is produced. In another embodiment, the method further comprises isolating SphK protein from the medium or the host cell.

Transgenic SphK Animals

The host cells of the invention can also be used to produce non-human transgenic animals. For example, in one embodiment, a host cell of the invention is a fertilized oocyte or an embryonic stem cell into which SphK protein-coding sequences have been introduced. Such host cells can then be used to create non-human transgenic animals in which exogenous SphK sequences have been introduced into their genome or homologous recombinant animals in which endogenous SphK sequences have been altered. Such animals are useful for studying the function and/or activity of SphK protein and for identifying and/or evaluating modulators of SphK protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous SphK gene has been altered by homologous recombination between the endogenous gene and an exogenous DNA molecule introduced into a cell of the animal, e.g., an embryonic cell of the animal, prior to development of the animal.

A transgenic animal of the invention can be created by introducing SphK-encoding nucleic acid into the male pronuclei of a fertilized oocyte (e.g., by microinjection, retroviral infection) and allowing the oocyte to develop in a pseudopregnant female foster animal. For example, the SphK cDNA sequence of SEQ ID NO:1 or 5 can be introduced as a transgene into the genome of a non-human animal. Alternatively, a non-human homologue of the human SphK gene, such as the SphK cDNA sequence of SEQ ID NO:3, 7, or 9, can be used as a transgene. Intronic sequences and polyadenylation signals can also be included in the transgene to increase the efficiency of expression of the transgene. A tissue-specific regulatory sequence(s) can be operably-linked to the SphK transgene to direct expression of SphK protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the SphK transgene in its genome and/or expression of SphK mRNA in tissues or cells of the animals. A transgenic founder animal can then be used to breed additional animals carrying the transgene. Moreover, transgenic animals carrying a transgene-encoding SphK protein can further be bred to other transgenic animals carrying other transgenes.

To create a homologous recombinant animal, a vector is prepared which contains at least a portion of an SphK gene into which a deletion, addition or substitution has been introduced to thereby alter, e.g., functionally disrupt, the SphK gene. The SphK gene can be a human gene (e.g., the cDNA of SEQ ID NO:1 or 5), but more preferably, is a non-human homologue of a human SphK gene. For example, a mouse homologue of human SphK gene can be used to construct a homologous recombination vector suitable for altering an endogenous SphK gene in the mouse genome. In one embodiment, the vector is designed such that, upon homologous recombination, the endogenous SphK gene is functionally disrupted (i.e., no longer encodes a functional protein; also referred to as a "knock out" vector).

Alternatively, the vector can be designed such that, upon homologous recombination, the endogenous SphK gene is mutated or otherwise altered but still encodes functional protein (e.g., the upstream regulatory region can be altered to thereby alter the expression of the endogenous SphK protein). In the homologous recombination vector, the altered portion of the SphK gene is flanked at its 5'- and 3'-termini by additional nucleic acid of the SphK gene to allow for homologous recombination to occur between the exogenous SphK gene carried by the vector and an endogenous SphK gene in an embryonic stem cell. The additional flanking SphK nucleic acid is of sufficient length for successful homologous recombination with the endogenous gene. Typically, several kilobases of flanking DNA (both at the 5'- and 3'-termini) are included in the vector. See, e.g., Thomas, et al., 1987. *Cell* 51: 503 for a description of homologous recombination vectors. The vector is then introduced into an embryonic stem cell line (e.g., by electroporation) and cells in which the introduced SphK gene has homologously-recombined with the endogenous SphK gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The SphK nucleic acid molecules, SphK proteins, and anti-SphK antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an SphK protein or anti-SphK antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The isolated nucleic acid molecules of the invention can be used to express SphK protein (e.g., via a recombinant expression vector in a host cell in gene therapy applications), to detect SphK mRNA (e.g., in a biological sample) or a genetic lesion in an SphK gene, and to modulate SphK activity, as described further, below. In addition, the SphK proteins can be used to screen drugs or compounds that modulate the SphK protein activity or expression as well as to treat disorders characterized by insufficient or excessive production of SphK protein or production of SphK protein forms that have decreased or aberrant activity compared to SphK wild-type protein. In addition, the anti-SphK antibodies of the invention can be used to detect and isolate SphK proteins and modulate SphK activity.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to SphK proteins or have a stimulatory or inhibitory effect on, e.g., SphK protein expression or SphK protein activity. The invention also includes compounds identified in the screening assays described herein.

In one embodiment, the invention provides assays for screening candidate or test compounds that bind to or modulate the activity of SphK protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell that has been engineered to express a membrane-bound form of an SphK protein, or a biologically-active portion thereof, on the cell surface is contacted with a test compound and the ability of the test compound to bind to an SphK protein determined. The cell, for example, can of mammalian origin or a yeast cell. Determining the ability of the test compound to bind to the SphK protein can be accomplished, for example, by coupling the test compound with a radioisotope or enzymatic label such that binding of the test compound to the SphK protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of SphK protein, or a biologically-active portion thereof, on the cell surface with a known compound which binds SphK to form an assay mixture, contacting the assay mixture with a test compound, and determining the ability of the test compound to interact with an SphK protein, wherein determining the ability of the test compound to interact with an SphK protein comprises determining the ability of the test compound to preferentially bind to SphK protein or a biologically-active portion thereof as compared to the known compound.

In another embodiment, an assay is a cell-based assay comprising contacting a cell engineered to express a membrane-bound form of SphK protein, or a biologically-active portion thereof, on the cell surface with a test compound and determining the ability of the test compound to modulate (e.g., stimulate or inhibit) the activity of the SphK protein or biologically-active portion thereof. Determining the ability of the test compound to modulate the activity of SphK or a biologically-active portion thereof can be accomplished, for example, by determining the ability of the SphK protein to phosphorylate sphingosine. Alternatively, the ability of SphK to bind a target molecule may be determined. As used herein, a "target molecule" is a molecule with which an SphK protein binds or interacts in nature. An SphK target molecule can be a non-SphK molecule or an SphK protein or polypeptide of the invention In one embodiment, an SphK target molecule is a component of a signal transduction pathway that facilitates transduction of an extracellular signal through the cell membrane and into the cell. The target, for example, can be a second intercellular protein that has catalytic activity or a protein that facilitates the association of downstream signaling molecules with SphK.

Determining the ability of the SphK protein to bind to or interact with an SphK target molecule can be accomplished by one of the methods described above for determining direct binding. In one embodiment, determining the ability of the SphK protein to bind to or interact with an SphK target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising an SphK-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting an SphK protein or biologically-active portion thereof with a test compound and determining the ability of the test compound to bind to the SphK protein or biologically-active portion thereof. Binding of the test compound to the SphK protein can be determined either directly or indirectly as described above. In one such embodiment, the assay comprises contacting the SphK protein or biologically-active portion thereof with a known compound which binds SphK to form an assay mixture, contacting the assay mixture with a test compound, and determining the ability of the test compound to interact with an SphK protein, wherein determining the ability of the test compound to interact with an SphK protein comprises determining the ability of the test compound to preferentially bind to SphK or biologically-active portion thereof as compared to the known compound.

In still another embodiment, an assay is a cell-free assay comprising contacting SphK protein or biologically-active portion thereof with a test compound and determining the ability of the test compound to modulate (e.g. stimulate or inhibit) the activity of the SphK protein or biologically-active portion thereof (e.g., the ability to phosphorylate sphingosine). Determining the ability of the test compound to modulate the activity of SphK can be accomplished, for example, by determining the ability of the SphK protein to bind to an SphK target molecule by one of the methods described above for determining direct binding. In an alternative embodiment, determining the ability of the test compound to modulate the activity of SphK protein can be accomplished by determining the ability of the SphK protein further modulate an SphK target molecule. For example, the catalytic/enzymatic activity of the target molecule on an appropriate substrate can be determined as described, supra.

In yet another embodiment, the cell-free assay comprises contacting the SphK protein or biologically-active portion thereof with a known compound which binds SphK protein to form an assay mixture, contacting the assay mixture with a test compound, and determining the ability of the test compound to interact with an SphK protein, wherein determining the ability of the test compound to interact with an SphK protein comprises determining the ability of the SphK protein to preferentially bind to or modulate the activity of an SphK target molecule.

In more than one embodiment of the above assay methods of the invention, it may be desirable to immobilize either SphK protein or its target molecule to facilitate separation of complexed from uncomplexed forms of one or both of the proteins, as well as to accommodate automation of the assay. Binding of a test compound to SphK protein, or interaction of SphK protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-SphK fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or SphK protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of SphK protein binding or activity determined using standard techniques.

Other techniques for immobilizing proteins on matrices can also be used in the screening assays of the invention. For example, either the SphK protein or its target molecule can be immobilized utilizing conjugation of biotin and streptavidin. Biotinylated SphK protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with SphK protein or target molecules, but which do not interfere with binding of the SphK protein to its target molecule, can be derivatized to the wells of the plate, and unbound target or SphK protein trapped in the wells by antibody conjugation. Methods for detecting such complexes, in addition to those described above for the GST-immobilized complexes, include immunodetection of complexes using antibodies reactive with the SphK protein or target molecule, as well as enzyme-linked assays that rely on detecting an enzymatic activity associated with the SphK protein or target molecule.

In another embodiment, modulators of SphK protein expression are identified in a method wherein a cell is contacted with a candidate compound and the expression of SphK mRNA or protein in the cell is determined. The level of expression of SphK mRNA or protein in the presence of the candidate compound is compared to the level of expression of SphK mRNA or protein in the absence of the candidate compound. The candidate compound can then be identified as a modulator of SphK mRNA or protein expression based upon this comparison. For example, when expression of SphK mRNA or protein is greater (i.e., statistically significantly greater) in the presence of the candidate compound than in its absence, the candidate compound is identified as a stimulator of SphK mRNA or protein expression. Alternatively, when expression of SphK mRNA or protein is less (statistically significantly less) in the presence of the candidate compound than in its absence, the candidate compound is identified as an inhibitor of SphK mRNA or protein expression. The level of SphK mRNA or protein expression in the cells can be determined by methods described herein for detecting SphK mRNA or protein.

In yet another aspect of the invention, the SphK proteins can be used as "bait proteins" in a two-hybrid assay or three hybrid assay (see, e.g., U.S. Pat. No. 5,283,317; Zervos, et al., 1993. Cell 72: 223–232; Madura, et al., 1993. J. Biol. Chem. 268: 12046–12054; Bartel, et al., 1993. Biotechniques 14: 920–924; Iwabuchi, et al., 1993. Oncogene 8: 1693–1696; and Brent WO 94/10300), to identify other proteins that bind to or interact with SphK ("SphK-binding proteins" or "SphK-bp") and modulate SphK activity. Such SphK-binding proteins are also likely to be involved in the propagation of signals by the SphK proteins as, for example, upstream or downstream elements of the SphK pathway.

The two-hybrid system is based on the modular nature of most transcription factors, which consist of separable DNA-binding and activation domains. Briefly, the assay utilizes two different DNA constructs. In one construct, the gene that codes for SphK is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an SphK-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with SphK.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the SphK sequences, SEQ ID NO:1, 3, 5, 7, or 9, can be used to map the location of the SphK genes, respectively, on a chromosome. The mapping of the SphK sequences to chromosomes is an important first step in correlating these sequences with genes associated with disease.

Briefly, SphK genes can be mapped to chromosomes by preparing PCR primers (preferably 15–25 bp in length) from the SphK sequences. Computer analysis of the SphK, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the SphK sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. *Science* 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the SphK sequences to design oligonucleotide primers, sub-localization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. *Nature,* 325: 783–787.

Moreover, differences in the DNA sequences between individuals affected and unaffected with a disease associated with the SphK gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The SphK sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the SphK sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue.

The human SphK sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NO:1, 3, 5, 7, or 9, are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining SphK protein and/or nucleic acid expression as well as SphK activity, in the context of a biological sample (e.g., blood, serum, cells, tissue) to thereby determine whether an individual is afflicted with a disease or disorder, or is at risk of developing a disorder, associated with aberrant SphK expression or activity. The disorders include cell proliferation disorders such as cancers, ischemia, or restenosis. The invention also provides for prognostic (or predictive) assays for determining whether an individual is at risk of developing a disorder associated with SphK protein, nucleic acid expression or activity. For example, mutations in an SphK gene can be assayed in a biological sample. Such assays can be used for prognostic or predictive purpose to thereby prophylactically treat an individual prior to the onset of a disorder characterized by or associated with SphK protein, nucleic acid expression, or biological activity.

Another aspect of the invention provides methods for determining SphK protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of SphK in clinical trials.

These and other agents are described in further detail in the following sections.

Diagnostic Assays

An exemplary method for detecting the presence or absence of SphK in a biological sample involves obtaining a biological sample from a test subject and contacting the biological sample with a compound or an agent capable of detecting SphK protein or nucleic acid (e.g., mRNA, genomic DNA) that encodes SphK protein such that the presence of SphK is detected in the biological sample. An agent for detecting SphK mRNA or genomic DNA is a labeled nucleic acid probe capable of hybridizing to SphK mRNA or genomic DNA. The nucleic acid probe can be, for example, a full-length SphK nucleic acid, such as the nucleic acid of SEQ ID NO:1, 3, 5, 7, or 9, or a portion thereof, such as an oligonucleotide of at least 15, 30, 50, 100, 250 or 500 nucleotides in length and sufficient to specifically hybridize under stringent conditions to SphK mRNA or genomic DNA. Other suitable probes for use in the diagnostic assays of the invention are described herein.

An agent for detecting SphK protein is an antibody capable of binding to SphK protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i. e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect SphK mRNA, protein, or genomic DNA in a biological sample in vitro as well as in vivo. For example, in vitro techniques for detection of SphK mRNA include Northern hybridizations and in situ hybridizations. In vitro techniques for detection of SphK protein include enzyme linked immunosorbent assays (ELISAs), Western blots, immunoprecipitations, and immunofluorescence. In vitro techniques for detection of SphK genomic DNA include Southern hybridizations. Furthermore, in vivo techniques for detection of SphK protein include introducing into a subject a labeled anti-SphK antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting SphK protein, mRNA, or genomic DNA, such that the presence of SphK protein, mRNA or genomic DNA is detected in the biological sample, and comparing the presence of SphK protein, mRNA or genomic DNA in the control sample with the presence of SphK protein, mRNA or genomic DNA in the test sample.

The invention also encompasses kits for detecting the presence of SphK in a biological sample. For example, the kit can comprise: a labeled compound or agent capable of detecting SphK protein or mRNA in a biological sample; means for determining the amount of SphK in the sample; and means for comparing the amount of SphK in the sample with a standard. The compound or agent can be packaged in a suitable container. The kit can further comprise instructions for using the kit to detect SphK protein or nucleic acid.

Prognostic Assays

The diagnostic methods described herein can furthermore be utilized to identify subjects having or at risk of developing a disease or disorder associated with aberrant SphK expression or activity. For example, the assays described herein, such as the preceding diagnostic assays or the following assays, can be utilized to identify a subject having or at risk of developing a disorder associated with SphK protein, nucleic acid expression or activity. Alternatively, the prognostic assays can be utilized to identify a subject having or at risk for developing a disease or disorder. Thus, the invention provides a method for identifying a disease or disorder associated with aberrant SphK expression or activity in which a test sample is obtained from a subject and SphK protein or nucleic acid (e.g., mRNA, genomic DNA) is detected, wherein the presence of SphK protein or nucleic acid is diagnostic for a subject having or at risk of developing a disease or disorder associated with aberrant SphK expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant SphK expression or activity. For example, such methods can be used to determine whether a subject can be effectively treated with an agent for a disorder. Thus, the invention provides methods for determining whether a subject can be effectively treated with an agent for a disorder associated with aberrant SphK expression or activity in which a test sample is obtained and SphK protein or nucleic acid is detected (e.g., wherein the presence of SphK protein or nucleic acid is diagnostic for a subject that can be administered the agent to treat a disorder associated with aberrant SphK expression or activity).

The methods of the invention can also be used to detect genetic lesions in an SphK gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an SphK protein, or the misexpression of the SphK gene. For example, such genetic lesions can be detected by ascertaining the existence of at least one of: (i) a deletion of one or more nucleotides from an SphK gene; (ii) an addition of one or more nucleotides to an SphK gene; (iii) a substitution of one or more nucleotides of an SphK gene, (iv) a chromosomal rearrangement of an SphK gene; (v) an alteration in the level of a messenger RNA transcript of an SphK gene, (vi) aberrant modification of an SphK gene, such as of the methylation pattern of the genomic DNA, (vii) the presence of a non-wild-type splicing pattern of a messenger RNA transcript of an SphK gene, (viii) a non-wild-type level of an SphK protein, (ix) allelic loss of an SphK gene, and (x) inappropriate post-translational modification of an SphK protein. As described herein, there are a large number of assay techniques known in the art that can be used for detecting lesions in an SphK gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the SphK gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to an SphK gene under conditions such that hybridization and amplification of the SphK gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); Qβ Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an SphK gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in SphK can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in SphK can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the SphK gene and detect mutations by comparing the sequence of the sample SphK with the corresponding wild-type (control) sequence. Examples of sequencing reactions include those based on techniques developed by Maxim and Gilbert, 1977. *Proc. Natl. Acad. Sci. USA* 74: 560 or Sanger, 1977. *Proc. Natl. Acad. Sci. USA* 74: 5463. It is also contemplated that any of a variety of automated sequencing procedures can be utilized when performing the diagnostic assays (see, e.g., Naeve, et al., 1995. *Biotechniques* 19: 448), including sequencing by mass spectrometry (see, e.g., PCT International Publication No. WO 94/16101; Cohen, et al., 1996. *Adv. Chromatography* 36: 127–162; and Griffin, et al., 1993. *Appl. Biochem. Biotechnol.* 38: 147–159).

Other methods for detecting mutations in the SphK gene include methods in which protection from cleavage agents is used to detect mismatched bases in RNA/RNA or RNA/DNA heteroduplexes. See, e.g., Myers, et al., 1985. *Science* 230: 1242. In general, the art technique of "mismatch cleavage" starts by providing heteroduplexes of formed by hybridizing (labeled) RNA or DNA containing the wild-type SphK sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in SphK cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis* 15: 1657–1662. According to an exemplary embodiment, a probe based on an SphK sequence, e.g., a wild-type SphK sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in SphK genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766; Cotton, 1993. *Mutat. Res.* 285: 125–144; Hayashi, 1992. *Genet. Anal. Tech. Appl.* 9: 73–79. Single-stranded DNA fragments of sample and control SphK nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. *Nature* 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an SphK gene.

Furthermore, any cell type or tissue in which SphK is expressed may be utilized in the prognostic assays described herein.

Pharmacogenomics

Agents, or modulators that have a stimulatory or inhibitory effect on SphK activity (e.g., SphK gene expression), as identified by a screening assay described herein can be administered to individuals to treat (prophylactically or therapeutically) disorders (The disorders include cell proliferative disorders such as cancers, ischemia, or restenosis. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of SphK protein, expression of SphK nucleic acid, or mutation content of SphK genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.*, 23: 983–985; Linder, 1997. *Clin. Chem.*, 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of SphK protein, expression of SphK nucleic acid, or mutation content of SphK genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an SphK modulator, such as a modulator identified by one of the exemplary screening assays described herein.

Monitoring of Effects During Clinical Trials

Monitoring the influence of agents (e.g., drugs, compounds) on the expression or activity of SphK (e.g., the ability to modulate aberrant cell proliferation and/or differentiation) can be applied not only in basic drug screening, but also in clinical trials. For example, the effectiveness of an agent determined by a screening assay as described herein to increase SphK gene expression, protein levels, or upregulate SphK activity, can be monitored in clinical trails of subjects exhibiting decreased SphK gene expression, protein levels, or downregulated SphK activity. Alternatively, the effectiveness of an agent determined by a screening assay to decrease SphK gene expression, protein levels, or downregulate SphK activity, can be monitored in clinical trails of subjects exhibiting increased SphK gene expression, protein levels, or upregulated SphK activity. In such clinical trials, the expression or activity of SphK and, preferably, other genes that have been implicated in, for example, a cellular proliferation or immune disorder can be used as a "read out" or markers of the immune responsiveness of a particular cell.

By way of example, and not of limitation, genes, including SphK, that are modulated in cells by treatment with an agent (e.g., compound, drug or small molecule) that modulates SphK activity (e.g., identified in a screening assay as described herein) can be identified. Thus, to study the effect of agents on cellular proliferation disorders, for example, in a clinical trial, cells can be isolated and RNA prepared and analyzed for the levels of expression of SphK and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of SphK or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an SphK protein, mRNA, or genomic DNA in the preadministration sample; (iii) obtaining one or more post-administration samples from the subject; (iv) detecting the level of expression or activity of the SphK protein, mRNA, or genomic DNA in the post-administration samples; (v) comparing the level of expression or activity of the SphK protein, mRNA, or genomic DNA in the pre-administration sample with the SphK protein, mRNA, or genomic DNA in the post administration sample or samples; and (vi) altering the administration of the agent to the subject accordingly. For example, increased administration of the agent may be desirable to increase the expression or activity of SphK to higher levels than detected, ie., to increase the effectiveness of the agent. Alternatively, decreased administration of the agent may be desirable to decrease expression or activity of SphK to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant SphK expression or activity. The disorders include cell proliferative disorders such as cancer, ischemia, and restenosis. These methods of treatment will be discussed more fully, below.

Disease and Disorders

Diseases and disorders that are characterized by increased (relative to a subject not suffering from the disease or disorder) levels or biological activity may be treated with therapeutics that antagonize (i.e., reduce or inhibit) activity. This decrease in activity may come about in a variety of ways, for example: (1) by decreasing the copies of the gene in the cell (amplifier); (2) by decreasing transcription of the SphK gene (transcription down-regulators); (3) by decreasing the translation of SphK mRNA into protein (translation down-regulators); or (4) by decreasing the activity of SphK itself (antagonists).

Expression of SphK inhibits apoptosis. Xia et al., *J. Biol Chem* Nov. 26, 1999;274(48):34499–505. Cancer cells expressing SphK avoid apoptosis and thus continue to proliferate. By inhibiting SphK activity in the cancer cells, apoptosis is induced and the cancer cells are destroyed. Essentially any cell proliferative disease or disorder that is dependent on SphK activity for cell survival or proliferation may be treated with an SphK activity inhibitor of the present invention. Examples include cell proliferation associated with vascular diseases, such as atherosclerosis or restenosis, with hyperplasia, or with cancers such as leukemia, lymphoma, ovarian cancer, breast cancer, lung cancer, colon cancer, testicular cancer, stomach cancer, or skin cancer. The cell proliferation may also be associated with angiogenesis. By preventing angiogenesis, the blood supply to a tumor may be diminished.

Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with therapeutics that increase (i.e., are agonists to) activity. This increase in activity may come about in a variety of ways, for example: (1) by increasing the copies of the gene in the cell (deamplifiers); (2) by increasing transcription of the SphK gene (transcription up-regulators); (3) by increasing the translation of SphK mRNA into protein (translation up-regulators); or (4) by increasing the activity of SphK itself (agonists).

In certain cells, decreased levels of SphK leads to apoptosis. In situations wherein cell survival or proliferation is desired, therapeutics that increase SphK activity are particularly useful. By increasing SphK activity in a cell, apoptosis is prevented. Cells that would otherwise be apoptotic are able to survive or proliferate. An example of a disease or disorder that may be treated with a therapeutic that increases SphK activity is ischemia, such as that associated with myocardial infarction. By promoting angiognesis, the therapeutic's effect provides blood flow to the ischemic area. The therapeutics may also be used to increase peripheral blood flow to a specific area (e.g., a wound or a transplanted tissue, organ, limb).

Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant SphK expression or activity, by administering to the subject an agent that modulates SphK expression or at least one SphK activity. Subjects at risk for a disease that is caused or contributed to by aberrant SphK expression or activity can be identified by, for example, any or a combination of diagnostic or prognostic assays as described herein. Administration of a prophylactic agent can occur prior to the manifestation of symptoms characteristic of the SphK aberrancy, such that a disease or disorder is prevented or, alternatively, delayed in its progression. Depending upon the type of SphK aberrancy, for example, an SphK agonist or SphK antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating SphK expression or activity for therapeutic purposes. The modulatory method of the invention involves contacting a cell with an agent that modulates one or more of the activities of SphK protein activity associated with the cell. An agent that modulates SphK protein activity can be an agent as described herein, such as a nucleic acid or a protein, a naturally-occurring cognate ligand of an SphK protein, a peptide, an SphK peptidomimetic, or other small molecule. In one embodiment, the agent stimulates one or more SphK protein activity. Examples of such stimulatory agents include active SphK protein and a nucleic acid molecule encoding SphK that has been introduced into the cell. In another embodiment, the agent inhibits one or more SphK protein activity. Examples of such inhibitory agents include antisense SphK nucleic acid molecules and anti-SphK antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of an SphK protein or nucleic acid molecule. In one embodiment, the method involves administering an agent (e.g., an agent identified by a screening assay described herein), or combination of agents that modulates (e.g., up-regulates or down-regulates) SphK expression or activity. In another embodiment, the method involves administering an SphK protein or nucleic acid molecule as therapy to compensate for reduced or aberrant SphK expression or activity.

Inhibition of SphK activity is desirable in situations in which SphK is abnormally upregulated and/or in which decreased SphK activity is likely to have a beneficial effect (e.g., to induce apoptosis). One example of such a situation is where a subject has a disorder characterized by aberrant cell proliferation and/or differentiation (e.g., cancer or immune associated disorders). Another example of such a situation is where the subject has a gestational disease (e.g., preclampsia).

Determination of the Biological Effect of the Therapeutic

In various embodiments of the invention, suitable in vitro or in vivo assays are performed to determine the effect of a specific therapeutic and whether its administration is indicated for treatment of the affected tissue.

In various specific embodiments, in vitro assays may be performed with representative cells of the type(s) involved in the patient's disorder, to determine if a given therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Invention

The SphK nucleic acids and proteins of the invention are useful in potential prophylactic and therapeutic applications implicated in a variety of disorders including, but not limited to: proliferative disorders such as cancers, ischemia, or restenosis.

As an example, a cDNA encoding the SphK protein of the invention may be useful in gene therapy, and the protein may be useful when administered to a subject in need thereof. By way of non-limiting example, the compositions of the invention will have efficacy for treatment of patients suffering from cancers, ischemia, or restenosis.

Both the novel nucleic acid encoding the SphK protein, and the SphK protein of the invention, or fragments thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies that immunospecifically-bind to the novel substances of the invention for use in therapeutic or diagnostic methods.

EXAMPLES

The following examples illustrate by way of non-limiting example various aspects of the invention.

Example 1

Human Ortholog of Mouse AF068748

The inventor was able to piece together a homolog of the mouse SphK described in Kohama et al. (Kohama T, Olivera A, Edsall L, Nagiec M M, Dickson R, Spiegel S. "Molecular cloning and functional characterization of murine SphK". J Biol Chem. Sep. 11, 1998;273(37):23722–8). Kohama et al. did not have conclusive data on where the mouse protein starts, even though they showed that the mouse cDNAs they obtained had SphKinase activity in vivo. However, no human sequence has been deposited for this enzyme in GenBank or Geneseq. In their paper, the authors have an aligment that shows part of a hypothetical human sequence. Here, the inventor obtained a virtual full-length human sequence with Kozak consensus.

Having the full-length human sequence permitted the inventor to establish where the start of the mouse protein occurs. The mouse homolog produced contains all the conserved regions the authors described in the paper.

Human SphK (Ortholog of Mouse AF068748)

This sequence was found while extending d010-107.9 (107.9) in job 6424-collagen gel 24 hr versus 4, annotated as human similar to Norway rat gber_ai237625 EST234187. This led to Arabidopsis O65419 and *C. Elegans* T10B11.2, both proteins having some homology to mouse SphK AF068748. This sequence may be the human ortholog of AF068748 (because of the known involvement of this protein in protecting human umbilical cord vascular endothelial cells (HUVECs) from apoptosis (J Biol Chem, Vol. 274, Issue 48, 34499–34505, Nov. 26, 1999). Similarities were sought using BlastN with this sequence against GenBankEST. Several human ESTs were identified that potentially code for the human ortholog: from 5' AI478197 (there is a repetitive sequence), D31133, AA026479, AA0232791, AA232646, AI769914, AI972156, and AA081152. These sequences were then capassembled in 2 groups, 5' (D31133, AA026479, AA0232791) and 3' (AI769914 and AA081152) groups and then the 2 groups were capassembled. In SEQCALLING™, 85667810 and 71311176 represent the 5' end. The capassembled sequence was fragmented. So the inventor seqextended using this sequence as backbone and used the frameshift locations (that in general were weak assembly regions) to generate the right frame. The nucleic acid sequence of this human SphK cDNA is provided in SEQ ID NO:1. This sequence has a correct Kozak methionine. The amino acid sequence of the human SphK encoded by the cDNA is provided in SEQ ID NO:2.

Kohama et al. were concerned that the 2 ESTs they worked with had no Kozak methionine. All available mouse ESTs were seqextended and the consensus has a Kozak methionine (it starts at the same met and differs with SPHK1a by a couple of amino acids). The nucleic acid sequence of the consensus mouse SphK cDNA is provided by SEQ ID NO:3. The amino acid sequence of the mouse SphK encoded by the consensus cDNA is provided in SEQ ID NO:4.

Example 2

Novel SphK

A novel gene fragment was differentially expressed using collagen gels at 24 hrs as compared to 4 hrs. AL096766 in HTG database Homo sapiens from clone 59H18 on chromosome 22 splicing 64154-64003, 63017-62954, 59856-59711, 53578-53504, 51333-51181, 47183-47078, 45371-45295, 43645-43440, 42070-41860, 39078-38779, 37032-36151. In this clone there is a putative gene fragment annotated as dA59H18.2 (novel protein similar to human, mouse, yeast, worm and plant (predicted) proteins) created by splicing together 43440 . . . 43645, 45295 . . . 45371, 47078 . . . 47183, 51181 . . . 51333, 53504 . . . 53578, 59711 . . . 59856, 62954 . . . 63017, 64003 . . . >64154). The isolation d010-107.9 (see Example 1) enabled the extension of the gene in the 3' region, adding 93aa residues. In Seqcalling, the inventor assembled 85336019 (covers bases 915 to 1491 and 1800 to end), 84585492 (bases 360 to 960) and 80432911 that encodes for the 5' region and start codon. The cDNA was constructed by splicing 64154-64003, 63017-62954, 59856-59711, 53578-53504, 51333-51181, 47183-47078, 45371-45295, 43645-43440, 42070-41860, 39078-38779, 37032-36151, editing by removing 37032 to 36151, and adding 80432911. The resulting nucleic acid sequence of this human SphK cDNA is provided in SEQ ID NO:5. The amino acid sequence of the human SphK encoded by this cDNA is provided in SEQ ID NO:6. This sequence extends the sequence deposited in GenBank as putative fragment peptide CAB62977 both at the NH and COOH termini for a total of 125aa (FIG. 1). The additions identify the actual start and add a further conserved region (C5) to the deposited sequence.

A rat ortholog, designated AI237625, of this human SphK was determined. This ortholog is encoded in EST234187 from normalized rat placenta, Bento Soares Rattus sp. cDNA clone RPLDB60 3' end, mRNA sequence. A nucleic acid sequence comprising a portion of the rat ortholog is provided by SEQ ID NO:7. The amino acid sequence encoded by this segment is provided by SEQ ID NO:8.

A mouse ortholog, designated 52180312, of this human SphK was determined. This ortholog is encoded in a 382 nt cDNA (mb14a02.yl Soares mouse p3NMF19.5 Mus musculus cDNA clone IMAGE:329354 5', mRNA sequence (ai536375: pvalue 6.2e-80)). A nucleic acid sequence comprising a portion of the mouse ortholog is provided by SEQ ID NO:9. The amino acid sequence encoded by this segement is provided by SEQ ID NO:10.

An alignment of the human, rat, and mouse orthologs is shown in FIG. 2.

Figure 3B:
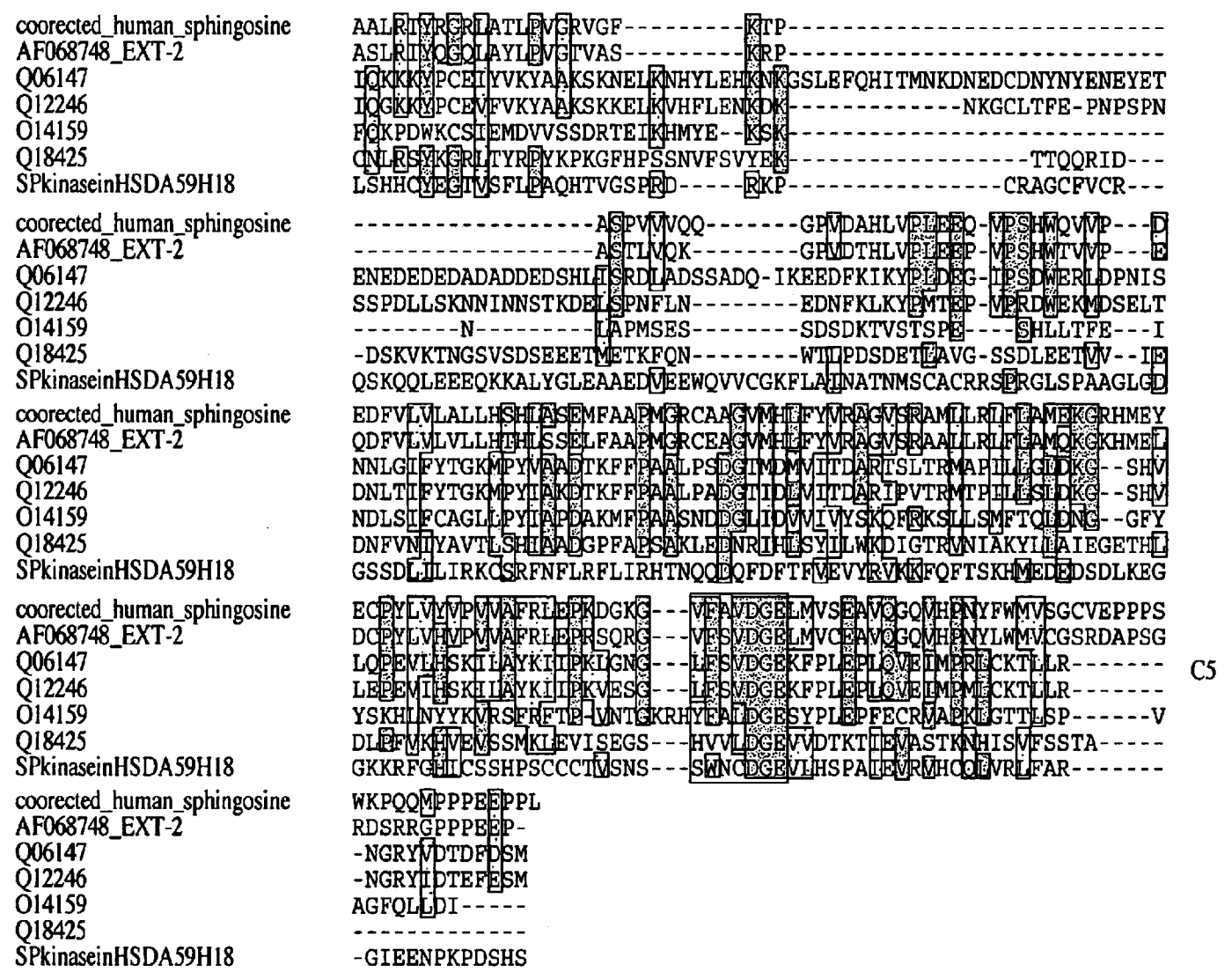

The alignment with the other human SphK, its mouse homolog, and homologs in other species clearly identified several conserved regions (FIG. 3), that were described in J Biol Chem. 1998 273:23722–8. The difference between the two human SphKs are in C3 and in C5, which finds a good homology to low density lipoprotein receptor. There is some homology to TGFB binding protein. At the C-terminus of the protein, there is some homology to granulins that have growth modulatory activity.

Psort puts this novel SphK in the endoplasmic reticulum, while the original human SphK (Example 1) is in the cytoplasm. Phylogenetic analysis indicates that this novel SphK is the founder of a new subfamily of SphKs (FIG. 4).

Comparing the putative translation of the Seqcalling assembly 80432911 with the sequence deposited in GenBank indicates the possibility of alternative splicing (FIG. 5).

Most of the sequences that went into Seqcalling assembly are from fetal tissues, some from brain or adrenal gland. It is possible that this SphK is normally only expressed during fetal development and then it is restricted to specific tissues. It could then be reactivated in tumors. It is contemplated that this novel enzyme may contribute part or all of the SphK activity in normal cells and/or in disease situations, potentially having a very important role in survival and motility of endothelial cells and tumor cells. Also, this novel SphK may serve as a small molecule drug target and antisense therapy target for angiogenesis related diseases.

The citation of any reference herein should not be deemed as an admission that such reference is available as prior art to the instant invention.

Equivalents

Although particular embodiments have been disclosed herein in detail, this has been done by way of example for purposes of illustration only, and is not intended to be limiting with respect to the scope of the appended claims which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims.

What is claimed is:

1. An isolated nucleic acid molecule comprising a nucleic acid sequence encoding a polypeptide comprising an amino acid sequence of SEQ ID NO:2, or the complete complement thereof.

2. The nucleic acid molecule of claim 1, wherein the nucleic acid molecule comprises a nucleic acid sequence having at least 80% nucleic acid sequence identity to the nucleic acid of SEQ ID NO:1.

3. The nucleic acid molecule of claim 1, wherein the nucleic acid molecule comprises a nucleic acid sequence having at least 85% nucleic acid sequence identity to the nucleic acid of SEQ ID NO:1.

4. The nucleic acid molecule of claim 1, wherein the nucleic acid molecule comprises a nucleic acid sequence having at least 90% nucleic acid sequence identity to the nucleic acid of SEQ ID NO:1.

5. The nucleic acid molecule of claim 1, wherein the nucleic acid molecule comprises a nucleic acid sequence having at least 95% nucleic acid sequence identity to the nucleic acid of SEQ ID NO:1.

6. The nucleic acid molecule of claim 1, wherein the nucleic acid molecule comprises a nucleic acid sequence of SEQ ID NO:1.

7. A vector comprising the nucleic acid molecule of claim 1.

8. The vector of claim 7, further comprising a promoter operably-linked to the nucleic acid molecule.

9. A cell comprising the vector of claim 7.

10. A composition comprising the nucleic acid molecule of claim 1 and a pharmaceutically-acceptable carrier.

11. A kit comprising in one or more containers, the composition of claim 10.

* * * * *

UNITED STATES PATENT AND TRADEMARK OFFICE
CERTIFICATE OF CORRECTION

PATENT NO. : 6,858,427 B2
DATED : February 22, 2005
INVENTOR(S) : Gerritsen et al.

It is certified that error appears in the above-identified patent and that said Letters Patent is hereby corrected as shown below:

Title page,
Item [56], References Cited, FOREIGN PATENT DOCUMENTS, insert the following in appropriate order:
-- EP         1074617        02/2001
   WO         WO 00/55332    09/2000
   WO         WO 00/70028    11/2000
   WO         WO 00/52173    09/2000
   WO         WO 01/31029    05/2001 --.
OTHER PUBLICATIONS, insert the following in appropriate order:
-- Wilson, R.K., Nov. 27, 1996, GenBank Accession No. AA232646 --.
"Orkin et al." reference, "Access the NIH Investment in Research on Gene Therapy, issued by the US NAtional Institutes" should read -- Assess the NIH Investment in Research on Gene Therapy, issued by the US National Institutes --.

Column 3,
Line 27, "to an disorders" should read -- to disorders --.
Line 54, "SphK plypeptide," should read -- SphK polypeptide, --.

Column 4,
Line 35, "SEQ ID 0NO: 12);" should read -- SEQ ID NO: 12); --.

Column 5,
Line 57, "the fall length" should read -- the full length --.

Column 7,
Lines 35-36, "between nucleotides units" should read -- between nucleotide units --.

Column 8,
Line 28, "rabbit, dog, cat" should read -- rabbit, dog, cat, --.

Column 10,
Line 56, "may corresponds to" should read -- may correspond to --.

Column 16,
Line 4, "1119-11124." should read -- 1119-1124. --.

Column 21,
Line 52, "analogs homologs" should read -- analogs, homologs --.

Column 30,
Line 13, "antibodies, may" should read -- antibodies, may be --.

UNITED STATES PATENT AND TRADEMARK OFFICE
CERTIFICATE OF CORRECTION

PATENT NO. : 6,858,427 B2
DATED : February 22, 2005
INVENTOR(S) : Gerritsen et al.

It is certified that error appears in the above-identified patent and that said Letters Patent is hereby corrected as shown below:

Column 52,
Line 60, "disorders (The disorders" should read -- disorders. The disorders --.

Column 54,
Line 14, "clinical trails" should read -- clinical trials --.

Column 60,
Line 41, "modifications considered" should read -- modifications are considered --.

Signed and Sealed this

Twenty-ninth Day of November, 2005

JON W. DUDAS
*Director of the United States Patent and Trademark Office*